US008796424B2

(12) United States Patent
Croasdale et al.

(10) Patent No.: US 8,796,424 B2
(45) Date of Patent: Aug. 5, 2014

(54) TRI- OR TETRASPECIFIC ANTIBODIES

(75) Inventors: Rebecca Croasdale, Antdorf (DE); Christian Klein, Bonstetten (CH); Wolfgang Schaefer, Mannheim (DE); Juergen Michael Schanzer, Traunstein (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 343 days.

(21) Appl. No.: 12/788,967

(22) Filed: May 27, 2010

(65) Prior Publication Data
US 2010/0322935 A1 Dec. 23, 2010

(30) Foreign Application Priority Data
May 27, 2009 (EP) .................................... 09007052

(51) Int. Cl.
*A61K 38/00* (2006.01)
(52) U.S. Cl.
USPC .................. 530/387.1; 424/133.1; 424/136.1
(58) Field of Classification Search
None
See application file for complete search history.

(56) References Cited

U.S. PATENT DOCUMENTS

| 5,202,238 | A | 4/1993 | Fell et al. | |
|---|---|---|---|---|
| 5,204,244 | A | 4/1993 | Fell et al. | |
| 6,602,684 | B1 | 8/2003 | Umana et al. | |
| 6,982,321 | B2 * | 1/2006 | Winter | 530/387.3 |
| 8,227,577 | B2 | 7/2012 | Klein et al. | |
| 8,242,247 | B2 * | 8/2012 | Klein et al. | 530/387.1 |
| 2005/0054048 | A1 | 3/2005 | Grasso et al. | |
| 2005/0152894 | A1 | 7/2005 | Krummen et al. | |
| 2006/0134709 | A1 | 6/2006 | Stavenhagen et al. | |
| 2009/0162359 | A1 * | 6/2009 | Klein et al. | 424/136.1 |
| 2009/0162360 | A1 | 6/2009 | Klein et al. | |
| 2009/0232811 | A1 | 9/2009 | Klein et al. | |
| 2010/0081796 | A1 * | 4/2010 | Brinkmann et al. | 530/387.3 |
| 2010/0111967 | A1 * | 5/2010 | Baehner et al. | 424/158.1 |
| 2012/0149879 | A1 * | 6/2012 | Brinkmann et al. | 530/387.3 |
| 2012/0164726 | A1 | 6/2012 | Klein et al. | |
| 2012/0225071 | A1 | 9/2012 | Klein et al. | |

FOREIGN PATENT DOCUMENTS

| CN | 101205255 A | 6/2008 |
|---|---|---|
| EP | 0307434 | 3/1989 |
| EP | 187049 A1 | 12/2007 |
| WO | WO 9409131 A1 * | 4/1994 |
| WO | 94/29350 | 12/1994 |
| WO | 95/09917 | 4/1995 |
| WO | 96/27011 | 9/1996 |
| WO | 97/28267 | 8/1997 |
| WO | 99/37791 | 7/1999 |
| WO | 99/54342 | 10/1999 |
| WO | WO 9966951 A2 * | 12/1999 |
| WO | 00/61739 | 10/2000 |
| WO | 01/77342 | 10/2001 |
| WO | 03/035835 A2 | 5/2003 |
| WO | 2004/065540 | 8/2004 |
| WO | 2005/011735 | 2/2005 |
| WO | 2005/018572 A2 | 3/2005 |
| WO | 2005/027966 | 3/2005 |
| WO | 2006/093794 | 9/2006 |
| WO | WO 2006093794 A1 * | 9/2006 |
| WO | 2006/103100 | 10/2006 |
| WO | 2006/114700 | 11/2006 |
| WO | 2006/116260 A2 | 11/2006 |
| WO | 2007/024715 | 3/2007 |
| WO | 2007/109254 | 9/2007 |
| WO | 2009/080251 | 7/2009 |
| WO | 2009/080252 | 7/2009 |
| WO | 2009/080253 | 7/2009 |
| WO | 2009/080254 | 7/2009 |
| WO | WO-2010/112193 A1 | 10/2010 |
| WO | WO-2010/145792 A1 | 12/2010 |
| WO | WO-2010/145792 A8 | 12/2010 |
| WO | WO-2010/145793 A1 | 12/2010 |

OTHER PUBLICATIONS

Merchant, et al. (Nature Biotechnology, 1998. vol. 16, pp. 677-681).*
Atwell et al., "Stable heterodimers from remodeling the domain interface of a homodimer using a phage display library" *J.Mol.Biol.* 270(1):26-35 (1997).
Barnes et al., "Advances in animal cell recombinant protein production: GS-NSO expression system" *Cytotechnology* 32(2):109-23 (Feb. 2000).
Barnes et al., "Characterization of the stability of recombinant protein production in the GS-NSO expression system" *Biotechnol Bioeng.* 73(4):261-70 (May 2001).
Boerner et al., "Production of Antigen-Specific Human Monoclonal Antibodies From in Vitro-Primed Human Splenocytes" *J Immunol.* 147(1):86-95 (Jul. 1991).
Bruggemann et al., "Comparison of the effector functions of human immunoglobulins using a matched set of chimeric antibodies" *J Exp Med.* 166(5):1351-61 (Nov. 1987).
Bruggemann, et al., "Designer Mice: The Production of Human Antibody Repertoires in Transgenic Animals" *Year in Immuno.* 7:33-40 (1993).
Brunhouse et al., "Isotypes of IgG: comparison of the primary structures of three pairs of isotypes which differ in their ability to activate complement" *Mol Immunol.* 16(11):907-17 (Nov. 1979).
Burton et al., "The C1q Receptor Site on Immunoglobulin G." *Nature* 288(5789):338-344 (Nov. 27, 1980).
Carter et al., "Humanization of an Anti-p185$^{HER}$ Antibody for Human Cancer Therapy" *Proc Natl Acad Sci U S A.* 89(10):4285-4289 (May 1992).
Cohen et al., "Nonchromosomal Antibiotic Resistance in Bacteria: Genetic Transformation of *Escherichia coli* by R-Factor DNA" Proc. Natl. Acad. Sci. USA 69(8):2110-2114 (Aug. 1972).
Cole et al., "The EBV-Hybridoma Technique and Its Application to Human Lung Cancer" *Monoclonal Antibodies and Cancer Therapy*, New York:Alan R. Liss, Inc. pp. 77-96 (1985).

(Continued)

*Primary Examiner* — Sean Aeder
*Assistant Examiner* — Julie Wu
(74) *Attorney, Agent, or Firm* — Morrison & Foerster LLP

(57) ABSTRACT

The present invention relates to tri- or tetraspecific antibodies, their manufacture and use.

26 Claims, 10 Drawing Sheets

(56) References Cited

OTHER PUBLICATIONS

Coloma and Morrison, "Design and production of novel tetravalent bispecific antibodies" *Nature Biotechnology* 15(2):159-163 (Feb. 1997).
*Current Protocols in Cell Biology* (reference not provided), Bonifacino et al., John Wiley & Sons, Inc. (2000).
*Current Protocols in Molecular Biology* (reference not provided), Ausubel at al., New York:Greene Publishing and Wiley Interscience (1987).74
Davies et al., "Expression of GnTIII in a Recombinant Anti-CD20 CHO Production Cell Line: Expression of Antibodies with Altered Glycoforms Leads to an Increase in ADCC Through Higher Affinity for FcγRIII" *Biotechnol. Bioeng.* 74:288-294 (2001).
Durocher et al., "High-level and high-throughput recombinant protein production by transient transfection of suspension-growing human 293-EBNA1 cells" *Nucleic Acids Research* 30(2 e9) (2002).
Edelman et al., "The covalent structure of an entire γG immunoglobulin molecule" *Proc. Natl. Acad. Sci. USA* 63:78-85 (1969)
Fischer et al., "Bispecific Antibodies: Molecules that Enable Novel Therapeutic Strategies" *Pathobiology* 74:3-14 (2007).
Geisse et al., "Eukaryotic Expression Systems: A Comparison" *Protein Expression and Purification* 8:271-282 (1996).
Graham et al., "A new technique for the assay of infectivity of human adenovirus 5 DNA" *Virology* 52(2):456-467 (1973).
Hezareh et al, "Effector Function Activities of a Panel- of Mutants of-a Broadly Neutralizing Antibody against Human Immunodeficiency Virus Type 1" *Journal of Virology* 75(24):12161-12168 (Dec. 2001).
Holliger et al., "Engineered antibody fragments and the rise of single domains" *Nat Biotechnol.* 23(9):1126-1136 (Sep. 2005).
Hoogenboom and Winter, "By-passing immunisation. Human antibodies from synthetic repertoires of germline $V_H$ gene segments rearranged in vitro" *J Mol Biol.* 227(2):381-388 (Sep. 20, 1992).
Idusogie et al., "Mapping of the C1q Binding Site on Rituxan, a Chimeric Antibody with a Human IgG1 Fc" *The Journal of Immunology* 164:4178-4184 (2000).
Jakobovits et al., "Analysis of Homozygous Mutant Chimeric Mice: Deletion of the Immunoglobulin Heavy-Chain Joining Region Blocks B-cell Development and Antibody Production" *Proc. Natl. Acad. Sci. USA* 90(6):2551-2555 (Mar. 15, 1993)
Jakobovits, et al., "Germ-line Transmission and Expression of a Human-derived Yeast Artificial Chromosome" *Nature* 362:255-258 (Mar. 1993).
Jefferis et al., "IgG-Fc-mediated effector functions: molecular definition of interaction sites for effector ligands and the role of glycosylation" *Immunol Rev.* 163:59-76 (1998).
Johnson et al., "Kabat Database and its applications: 30 years after the first variability plot" *Nucleic Acids Research* 28(1):214-218 (2000).
Kabat et al., "Evolutionary and structural influences on light chain constant (C/subL/nor) region of human and mouse immunoglobulins" *Proc. Natl. Acad. Sci. USA* 72(7):2785-2788 (Jul. 1975).
Kabat et al., *Sequences of Proteins of Immunological Interest* (Table of Contents and Introduction), 5th edition, Bethesda, MD:Public Health Service, NIH vol. 1 (1991).
Kaufman, R.J., "Overview of Vector Design for Mammalian Gene Expression" *Molecular Biotechnology* 16:151-161 (2000).
Kobayshi et al., "Similarities in the Biodistribution of Iodine-Labeled Anti-Tac Single-Chain Disulfide-Stabilized Fv Fragment and Anti-Tac Disulfide-Stabilized Fv Fragment" *Nuclear Medicine & Biology* 25:387-393 (1998).
Lifely et al., "Glycosylation and Biological Activity of CAMPATH-1H Expressed in Different Cell Lines and Grown Under Different Culture Conditions." *Glycobiology* 5(8):813-822 (Dec. 1995).
Love et al, "Recombinant antibodies possessing novel effector functions" *Methods in Enzymology* 178:515-527 (1989).

Lukas et al., "Inhibition of C1-Mediated Immune Hemolysis by Monomeric and Dimeric Peptides from the Second Constant Domain of Human Immunoglobulin $G^1$" *The Journal of Immunology* 127(6):2555-2560 (Dec. 1981).
Lund et al., "Oligosaccharide-protein interactions in IgG can modulate recognition by Fcγ receptors" *FASEB Journal* 9:115-119 (1995).
Makrides, S.C., "Components of Vectors for Gene Transfer and Expression in Mammalian Cells" *Protein Expression and Purification* 17:183-202 (1999).
Marks et al., "By-Passing Immunization: Human Antibodies From V-gene Libraries Di-splayed on Phage" *J Mol Biol.* 222(3):581-597 (Dec. 5, 1991).
Meissner et al., "Transient Gene Expression: Recombinant Protein Production with Suspension-Adapted HEK293-EBNA Cells" *Biotechnology and Bioengineering* 75:197-203 (2001).
Merchant et al., "An efficient route to human bispecific IgG" *Nature Biotechnology* 16(7):677-681 (1998).
Milstein and Cuello, "Hybrid Hybridomas and Their Use in Immunohistochemistry" *Nature* 305:537-540 (Oct. 6, 1983).
Mimura et al., "Role of Oligosaccharide Residues of IgG1-Fc in FcγRIIb Binding" *The Journal of Biological Chemistry* 276(49):45539-45547 (Dec. 7, 2001).
Morgan et al., "The N-terminal End of the $C_H2$ Domain of Chimeric Human IgG1 anti-HLA-DR is Necessary for C1q, FcγRI and FcγRIII Binding" *Immunology* 86:319-324 (1995).
Morrison et al., "Variable Region Domain Exchange Influences the Functional Properties of $IgG^1$" *J. of Immunology* 160 :2802-2808 (1998).
Morrison et al., "Chimeric Human Antibody Molecules: Mouse Antigen-Binding Domains with Human Constant Region Domains" *Proc. Natl. Acad. Sci. USA* 81(21):6851-6855 (Nov. 1984).
Morrison, S.L., "Two Heads are Better than One" *Nature Biotechnology* 25(11):1233-1234 (Nov. 2007).
Neuberger et al., "A hapten-specific chimaeric IgE antibody with human physiological effector function" *Nature* 314:268-270 (Mar. 21, 1985).
Norderhaug et al., "Versatile Vectors for Transient and Stable Expression of Recombinant Antibody Molecules in Mammalian Cells" *Journal of Immunological Methods* 204:77-87 (1997).
Orlandi et al., "Cloning Immunoglobulin Variable Domains for Expression by the Polymerase Chain Reaction" *Proc. Natl. Acad. Sci. USA* 86:3833-3837 (May 1989).
Pace et al., "How to Measure and Predict the Molar Absorption Coefficient of a Protein" *Protein Science* 4(11):2411-2423 (Nov. 1995).
Radaev et al., "Recognition of IgG by Fcγ Receptor" *The Journal of Biological Chemistry* 276(19):16478-16483 (May 11, 2001).
Rajagopal et al., "A Form of Anti-Tac(Fv) Which is Both Single-chain and Disulfide Stabilized: Comparison with its Single-chain and Disulfide-stabilized Homologs" *Protein Engineering* 10(12):1453-1459 (1997).
Raju, T.S., "Glycosylation Variations with Expression Systems and Their Impact on Biological Activity of Therapeutic Immunoglobulins" *BioProcess International* 1(4):44-53 (Apr. 2003).
Ridgway et al., "'Knobs-into-holes' Engineering of Antibody $C_H3$ Domains for Heavy Chain Heterodimerization" *Protein Engineering* 9(7):617-621 (1996).
Riechmann et al., "Reshaping Human Antibodies for Therapy" *Nature* 332:323-327 (Mar. 24, 1988).
Routier et al., "The Glycosylation Pattern of a Humanized IgGI Antibody (D1.3) Expressed in CHO Cells" *Glycoconjugate Journal* 14:201-207 (1997).
Schlaeger et al., "Transient Gene Expression in Mammalian Cells Grown in Serum-free Suspension Culture" *Cytotechnology* 30:71-83 (1999).
Schlaeger, E., "The Protein Hydrolysate, Primatone RL, is a Cost-effective Multiple Growth Promoter of Mammalian Cell Culture in Serum-containing and Serum-free Media and Displays Anti-apoptosis Properties" *Journal of Immunological Methods* 194:191-199 (1996).

(56) References Cited

OTHER PUBLICATIONS

Schmidt et al., "Suppression of—Metastasis Fomation by a Recombinant Single Chain Antibody-toxin Targeted to Full-length and Oncogenic Variant EGF Receptors" *Oncogene* 18:1711-1721 (1999).

Shen et al., "Single Variable Domain Antibody as a Versatile Building Block for the Construction of IgG-like Bispecific Antibodies" *Jounal of Immunological* 318:65-74 (2007).

Shields et al., "High Resolution Mapping of the Binding Site on Human IgG1 for FcγRI, FcγRII, FcγRIII, and FcRn and Design of IgG1 Variants with Improved Binding to the FcγR" *Journal of Biological Chemistry* 276(9):6591-6604 (2001).

Shields et al., "Lack of Fucose on Human IgG1 N-Linked Oligosaccharide Improves Binding to Human FcγRIII and Antibody-dependent Cellular Toxicity" *J Biol Chem.* 277(30):26733-26740 (Jul. 26, 2002).

Simmons, L. et al., "Expression of full-length immunoglobulins in *Escherichia coli*: Rapid and efficient production of aglycosylated antibodies" *Journal of Immunological Methods* 263:133-147 (2002).

Simon et al., "Antibody Domain Mutants Demonstrate Autonomy of the Antigen Binding Site" *The EMBO Journal* 9(4):1051-1056 (1990).

Thommesen et al., "Lysine 322 in the Human IgG3 C/subH/nor2 Domain is Crucial for Antibody Dependent Complement Activation" *Molecular Immunology* 37:995-1004 (2000).

Umana et al., "Engineered Glycoforms of an Antineuroblastoma IgG1 with Optimized Antibody-Dependent Cellular Cytotoxic Activity" *Nature Biotechnology* 17(2):176-180 (Feb. 1999).

van Dijk and van de Winkel, "Human antibodies as next generation therapeutics" *Curr Opin Chem Biol.* 5(4):368-74 (Aug. 2001).

Vijayalakshmi, M., "Antibody Purification Methods" *Applied Biochemistry and Biotechnology* 75:93-102 (1998).

Werner et al., "Appropriate Mammalian Expression Systems for Biopharmaceuticals" *Drug Research* 48(8):870-880 (1998).

Willems et al., "Optimizing Expression and Purification from Cell Culture Medium of Trispecific Recombinant Antibody Derivatives" *Journal of Chromatography B* 786:161-176 (2003).

Wright and Morrison, "Effect of Glycosylation on Antibody Function: Implications for Genetic Engineering" *Trends in Biotechnology* 15:26-32 (1997).

Wu et al., "Simultaneous Targeting of Multiple Disease Mediators by a Dual-Variable-Domain Immunoglobulin" *Nature Biotechnology* 25(11):1290-1297 (Nov. 2007).

\* cited by examiner

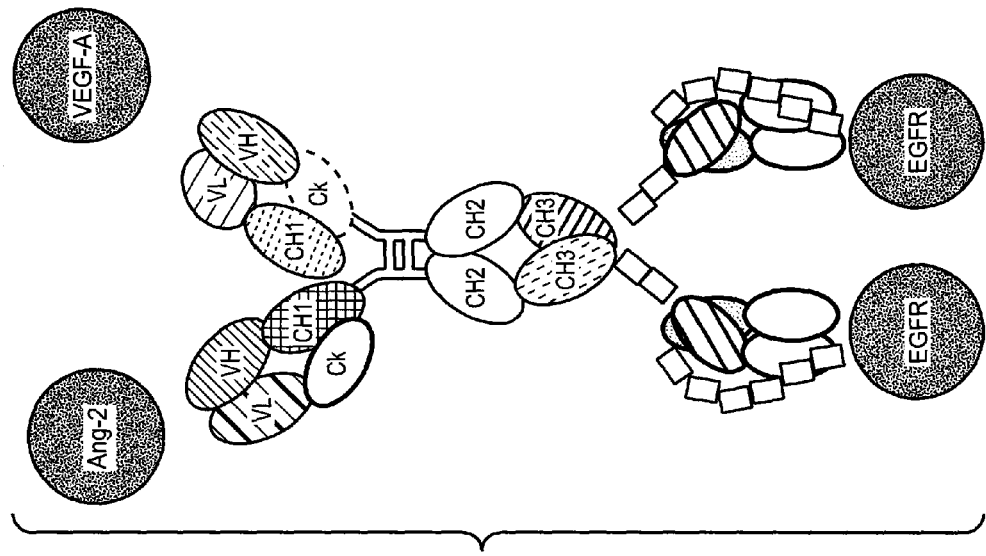
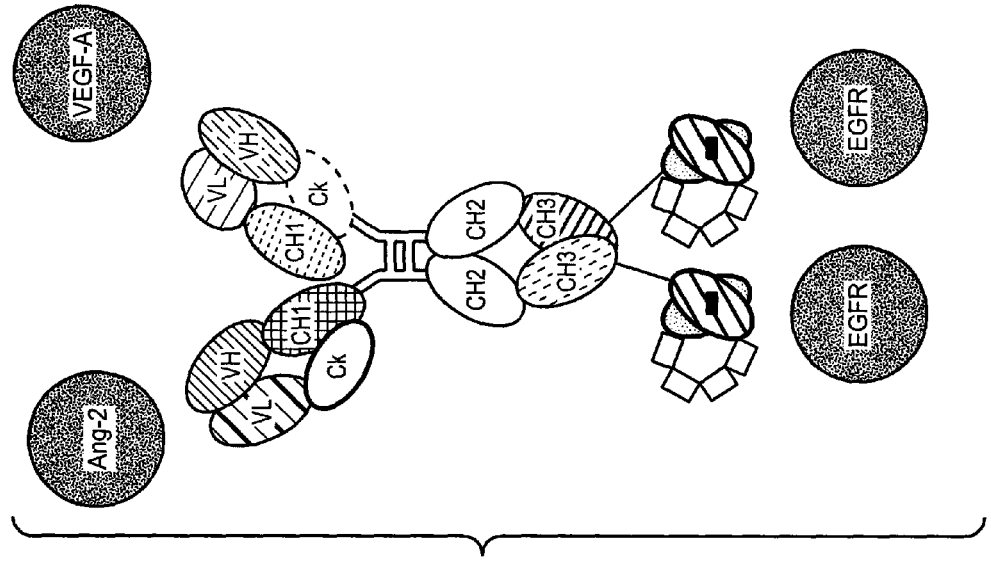
FIG. 5b
FIG. 5a

TRI- OR TETRASPECIFIC ANTIBODIES

CROSS-REFERENCE TO RELATED APPLICATIONS

This application claims benefit of priority under 35 USC §119(a) to European patent application number 9007052.5, filed 27 May 2009, the contents of which are incorporated herein by reference.

BACKGROUND OF THE INVENTION

Engineered proteins, such as bi- or multispecific antibodies capable of binding two or more antigens are known in the art. Such multispecific binding proteins can be generated using cell fusion, chemical conjugation, or recombinant DNA techniques.

A wide variety of recombinant multispecific antibody formats have been developed in the recent past, e.g. tetravalent bispecific antibodies by fusion of, e.g. an IgG antibody format and single chain domains (see e.g. Coloma, M. J., et. al., Nature Biotech. 15 (1997) 159-163; WO 2001/077342; and Morrison, S. L., Nature Biotech. 25 (2007) 1233-1234.

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech. 23 (2005) 1126-1136; Fischer, N., and Léger, O., Pathobiology 74 (2007) 3-14; Shen, J., et al., J. Immunol. Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFv (Fischer, N., and Léger, O., Pathobiology 74 (2007) 3-14). While it is obvious that linkers have advantages for the engineering of bispecific antibodies, they may also cause problems in therapeutic settings. Indeed, these foreign peptides might elicit an immune response against the linker itself or the junction between the protein and the linker. Furthermore, the flexible nature of these peptides makes them more prone to proteolytic cleavage, potentially leading to poor antibody stability, aggregation and increased immunogenicity. In addition one may want to retain effector functions, such as e.g. complement-dependent cytotoxicity (CDC) or antibody dependent cellular cytotoxicity (ADCC), which are mediated through the Fc-part by maintaining a high degree of similarity to naturally occurring antibodies.

Thus, ideally, one should aim at developing bispecific antibodies that are very similar in general structure to naturally occurring antibodies (like IgA, IgD, IgE, IgG or IgM) with minimal deviation from human sequences.

In one approach bispecific antibodies that are very similar to natural antibodies have been produced using the quadroma technology (see Milstein, C., and Cuello, A. C., Nature, 305 (1983) 537-40) based on the somatic fusion of two different hybridoma cell lines expressing murine monoclonal antibodies with the desired specificities of the bispecific antibody. Because of the random pairing of two different antibody heavy and light chains within the resulting hybrid-hybridoma (or quadroma) cell line, up to ten different antibody species are generated of which only one is the desired, functional bispecific antibody. Due to the presence of mispaired byproducts, and significantly reduced production yields, sophisticated purification procedures are required (see e.g. Morrison, S. L., Nature Biotech. 25 (2007) 1233-1234). In general the same problem of mispaired by-products remains if recombinant expression techniques are used.

An approach to circumvent the problem of mispaired byproducts, which is known as 'knobs-into-holes', aims at forcing the pairing of two different antibody heavy chains by introducing mutations into the CH3 domains to modify the contact interface. On one chain bulky amino acids were replaced by amino acids with short side chains to create a 'hole'. Conversely, amino acids with large side chains were introduced into the other CH3 domain, to create a 'knob'. By coexpressing these two heavy chains (and two identical light chains, which have to be appropriate for both heavy chains), high yields of heterodimer formation ('knob-hole') versus homodimer formation ('hole-hole' or 'knob-knob') was observed (Ridgway, J. B., et al., Protein Eng. 9 (1996) 617-621; and WO 96/027011). The percentage of heterodimer could be further increased by remodeling the interaction surfaces of the two CH3 domains using a phage display approach and the introduction of a disulfide bridge to stabilize the heterodimers (Merchant, A. M., et al., Nature Biotech. 16 (1998) 677-681; Atwell, S., et al., J. Mol. Biol. 270 (1997) 26-35). New approaches for the knobs-into-holes technology are described in e.g. EP 1 870 459 A1. Although this format appears very attractive, no data describing progression towards the clinic are currently available. One important constraint of this strategy is that the light chains of the two parent antibodies have to be identical to prevent mispairing and formation of inactive molecules. Thus, this technique is not appropriate as a basis for easily developing recombinant, tri- or tetraspecific antibodies against three or four antigens starting from two antibodies against the first and the second antigen, as either the heavy chains of these antibodies and/or the identical light chains have to be optimized first and then further antigen binding peptides against the third and fourth antigen have to be added.

WO 2006/093794 relates to heterodimeric protein binding compositions. WO 99/37791 describes multipurpose antibody derivatives. Morrison, S. L., et al., J. Immunol. 160 (1998) 2802-2808 refers to the influence of variable region domain exchange on the functional properties of IgG.

All references cited herein, including patent applications and publications, are incorporated by reference in their entirety.

SUMMARY OF THE INVENTION

The invention relates to a trispecific or tetraspecific antibody, comprising:
 a) a light chain and heavy chain of a full length antibody which specifically binds to a first antigen; and
 b) a modified light chain and modified heavy chain of a full length antibody which specifically binds to a second antigen, wherein the variable domains VL and VH are replaced by each other, and/or wherein the constant domains CL and CH1 are replaced by each other; and
 c) one to four antigen binding peptides which specifically bind to one or two further antigens fused via a peptide connector to the C- or N-terminus of the light chains or heavy chains of a) and/or b).

A further embodiment of the invention is a method for the preparation of a trispecific or tetraspecific antibody according to the invention comprising the steps of:
 a) transforming a host cell with vectors comprising nucleic acid molecules encoding
  aa) a light chain and heavy chain of an antibody which specifically binds to a first antigen; and ab) a modified light chain and modified heavy chain of a full length antibody which specifically binds to a second antigen, wherein the variable domains VL and VH are replaced by each other, and/or wherein the constant domains CL and CH1 are replaced by each other; and ac) one to four antigen binding peptides which specifically bind to one or two further antigens are fused via a peptide connector to the C- or N-terminus of the light chains or heavy chains of aa) and/or ab).

b) culturing the host cell under conditions that allow synthesis of said antibody; and c) recovering said antibody from said culture.

A further embodiment of the invention is a host cell comprising vectors comprising nucleic acid molecules encoding a) a light chain and heavy chain of an antibody which specifically binds to a first antigen; and b) a modified light chain and modified heavy chain of a full length antibody which specifically binds to a second antigen, wherein the variable domains VL and VH are replaced by each other, and/or wherein the constant domains CL and CH1 are replaced by each other; and c) wherein one to four antigen binding peptides which specifically bind to one or two further antigens are fused via a peptide connector to the C- or N-terminus of the light chains or heavy chains of a) and/or b)

A further embodiment of the invention is a composition, preferably a pharmaceutical or a diagnostic composition of the antibody according to the invention.

A further embodiment of the invention is a pharmaceutical composition comprising an antibody according to the invention and at least one pharmaceutically acceptable excipient.

A further embodiment of the invention is a method for the treatment of a patient in need of therapy, characterized by administering to the patient a therapeutically effective amount of an antibody according to the invention.

According to the invention, the ratio of a desired trispecific or tetraspecific antibody compared to undesired side products can be improved by the replacement of certain domains in only the pair of heavy chain and light chain (HC/LC) of the full length antibody which specifically binds to the second antigen (the second antibody). In this way the undesired mispairing of the light chain with the wrong heavy chain can be reduced (e.g., light chain of the first antibody with heavy chain of the second antibody or light chain of second antibody with heavy chain of the first antibody).

DESCRIPTION OF THE FIGURES

FIG. 5a Schematic structure of a trispecific antibody according to the invention recognizing Angiopoietin-2, VEGF-A and EGFR, which is tetravalent and uses disulfide stabilized single chain Fv fragments as antigen binding peptides (Example 2)

FIG. 5b Schematic structure of a trispecific antibody according to the invention recognizing Angiopoietin-2, VEGF-A and EGFR, which is tetravalent and uses single chain Fab fragments as antigen binding peptides (Example 2)

DETAILED DESCRIPTION OF THE INVENTION

Figure 1:
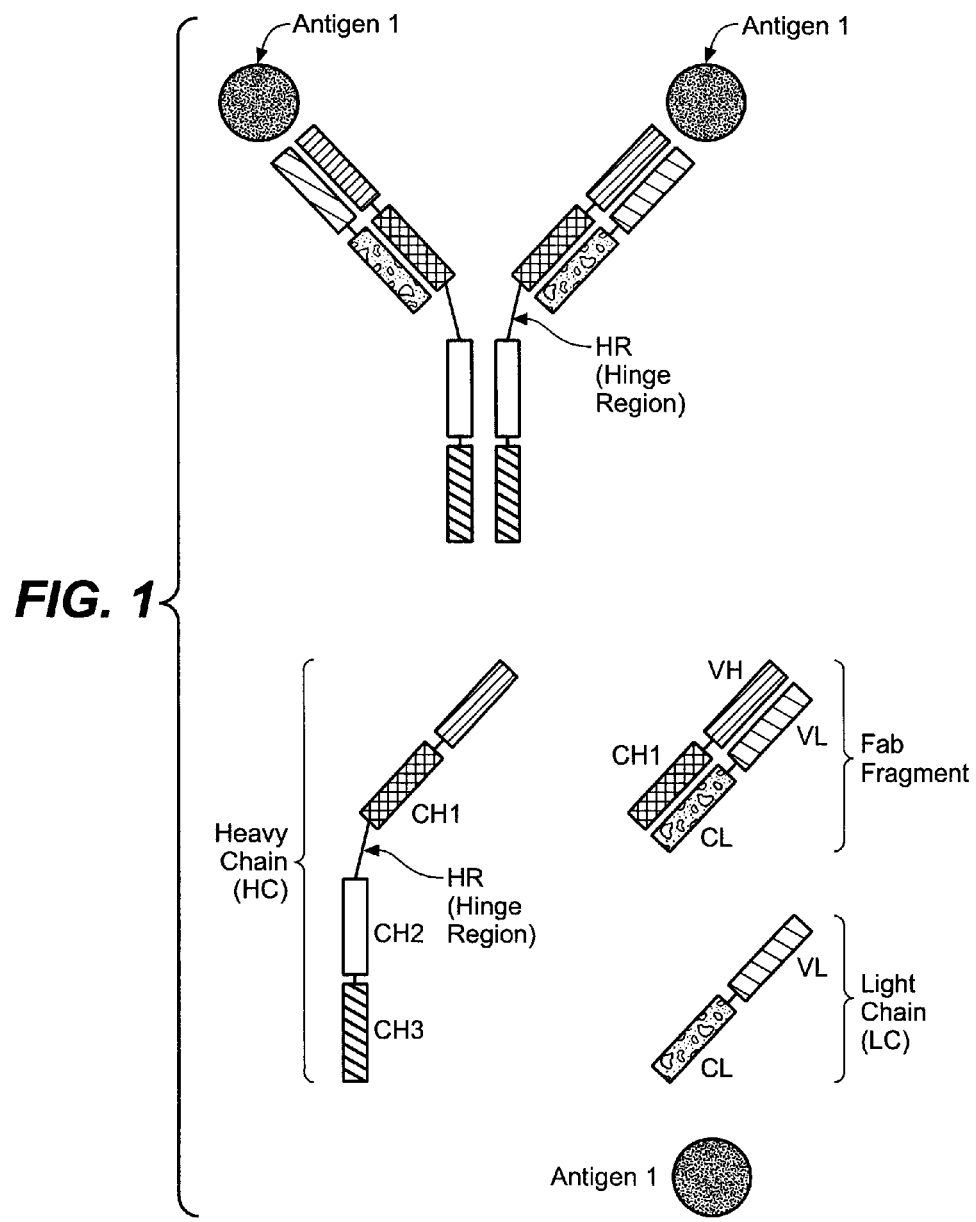
FIG. 1 Schematic structure of a full length antibody without CH4 domain specifically binding to a first antigen 1 with two pairs of heavy and light chain which comprise variable and constant domains in a typical order.

The invention relates to a trispecific or tetraspecific antibody, comprising:

a) a light chain and heavy chain of a full length antibody which specifically binds to a first antigen; and b) a modified light chain and modified heavy chain of a full length antibody which specifically binds to a second antigen, wherein the variable domains VL and VH are replaced by each other, and/or wherein the constant domains CL and CH1 are replaced by each other; and c) one to four antigen binding peptides which specifically bind to one or two further antigens fused via a peptide connector to the C- or N-terminus of the light chains or heavy chains of a) and/or b)

In one embodiment of the invention the trispecific or tetraspecific antibody according to the invention comprises under c) one or two antigen binding peptides which specifically bind to one or two further antigens.

In one embodiment of the invention the trispecific or tetraspecific antibody according to the invention is characterized in that the antigen binding peptides are selected from the group of a scFv fragment and a scFab fragment.

In one embodiment of the invention the trispecific or tetraspecific antibody according to the invention is characterized in that the antigen binding peptide(s) is/are scFv fragment(s).

In one embodiment of the invention the trispecific or tetraspecific antibody according to the invention is characterized in that the antigen binding peptide(s) is/are scFab fragment(s).

In one embodiment of the invention the trispecific or tetraspecific antibody according to the invention is characterized in that the antigen binding peptides are fused to the C-terminus of the heavy chains of a) and/or b).

In one embodiment of the invention the trispecific or tetraspecific antibody according to the invention comprises under c) one or two antigen binding peptides which specifically bind to one further antigen.

In one embodiment of the invention the trispecific or tetraspecific antibody according to the invention comprises under c) two identical antigen binding peptides which specifically bind to a third antigen or epitope. Preferably such two identical antigen binding peptides are fused both via a peptide connector to the C-terminus of a heavy chains of a) and/or b). Preferably said two identical antigen binding peptides are either a scFv fragment or a scFab fragment. Preferably each peptide connector has an identical amino acid sequence to the other(s).

In one embodiment of the invention, the trispecific or tetraspecific antibody according to the invention comprises under c) two antigen binding peptides which specifically bind to a third and a fourth antigen or epitope. In one embodiment said two antigen binding peptides are fused both via a peptide connector to the C-terminus of the heavy chains of a) and b). Preferably said two antigen binding peptides are either a scFv fragment or a scFab fragment. Preferably each peptide connector has an identical amino acid sequence to the other(s).

According to the invention, the ratio of a desired trispecific or tetraspecific antibody compared to undesired side products (due to mispairing of the light chain with the "wrong" heavy chain of the antibody which specifically binds to the other antigen) can be improved by the replacement of certain domains in only one pair of heavy chain and light chain (HC/LC). While the first of the two full length HC/LC pairs originates from an antibody which specifically binds to a first antigen and is left essentially unchanged, the second of the two full length HC/LC pairs originates from an antibody which specifically binds to a second antigen, and is modified by the following replacement:

light chain: replacement of the variable light chain domain, VL, by the variable heavy chain domain, VH, of said antibody which specifically binds to a second antigen, and/or the constant light chain domain, CL, by the constant heavy chain domain, CH1, of said antibody which specifically binds to a second antigen, and heavy chain: replacement of the variable heavy chain domain, VH, by the variable light chain domain, VL, of said antibody which specifically binds to a second antigen, and/or the constant heavy chain domain, CH1, by the constant light chain domain, CL, of said antibody which specifically binds to a second antigen.

To this ratio improved bispecific antibody then one to four antigen binding peptides which specifically bind to one or two further antigens are fused via a peptide connector to the C- or N-terminus of the light chains or heavy chains of said two antibodies which specifically bind to the first and second antigen resulting in the trispecific and tetraspecific antibody according to the invention.

Thus the resulting trispecific and tetraspecific antibody according to the invention are artificial antibodies which comprise a) a light chain and heavy chain of an antibody which specifically binds to a first antigen; and b) a light chain and heavy chain of an antibody which specifically binds to a second antigen,
wherein said light chain (of an antibody which specifically binds to a second antigen) contains a variable domain VH instead of VL
and/or a constant domain CH1 instead of CL
wherein said heavy chain (of an antibody which specifically binds to a second antigen) contains a variable domain VL instead of VH
and/or a constant domain CL instead of CH1.

In an additional aspect of the invention such improved ratio of a desired bivalent, bispecific antibody compared to undesired side products can be further improved by modifications of the CH3 domains of said full length antibodies which specifically bind to a first and second antigen within the tri- or tetraspecific antibody.

Thus in one preferred embodiment of the invention the CH3 domains of said tri- or tetraspecific antibody (in the heavy chain and in the modified heavy) according to the invention can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerisation of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

Thus in one aspect of the invention said trispecific or tetraspecific antibody is further characterized in that
the CH3 domain of the heavy chain of the full length antibody of a) and the CH3 domain of the modified heavy chain of the full length antibody of b) each meet at an interface which comprises an original interface between the antibody CH3 domains;
wherein said interface is altered to promote the formation of the trispecific or tetraspecific antibody, wherein the alteration is characterized in that:

i) the CH3 domain of one heavy chain is altered,
so that within the original interface the CH3 domain of one heavy chain that meets the original interface of the CH3 domain of the other heavy chain within the tri- or tetraspecific antibody,
an amino acid residue is replaced with an amino acid residue having a larger side chain volume, thereby generating a protuberance within the interface of the CH3 domain of one heavy chain which is positionable in a cavity within the interface of the CH3 domain of the other heavy chain and ii) the CH3 domain of the other heavy chain is altered,
so that within the original interface of the second CH3 domain that meets the original interface of the first CH3 domain within the tri- or tetraspecific antibody an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

In one aspect of the invention both CH3 domains are further altered by the introduction of a cysteine (C) residue in positions of each CH3 domain such that a disulfide bridge between the CH3 domains can be formed.

In one preferred embodiment, said trispecific or tetraspecific antibody comprises a T366W mutation in the CH3 domain of the "knobs chain" and T366S, L368A, Y407V mutations in the CH3 domain of the "hole chain". An additional interchain disulfide bridge between the CH3 domains can also be used (Merchant, A. M., et al., Nature Biotech. 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, said trispecific or tetraspecific antibody comprises Y349C, T366W mutations in one of the two CH3 domains and E356C, T366S, L368A, Y407V mutations in the other of the two CH3 domains or said trispecific or tetraspecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering always according to EU index of Kabat). But also other knobs-in-holes technologies as described by EP 1 870 459A1, can be used alternatively or additionally. A preferred example for said trispecific or tetraspecific antibody are R409D; K370E mutations in the CH3 domain of the "knobs chain" and D399K; E357K mutations in the CH3 domain of the "hole chain" (numbering always according to EU index of Kabat).

In another preferred embodiment said trispecific or tetraspecific antibody comprises a T366W mutation in the CH3 domain of the "knobs chain" and T366S, L368A, Y407V mutations in the CH3 domain of the "hole chain" and additionally R409D; K370E mutations in the CH3 domain of the "knobs chain" and D399K; E357K mutations in the CH3 domain of the "hole chain".

In another preferred embodiment said trispecific or tetraspecific antibody comprises Y349C, T366W mutations in one of the two CH3 domains and S354C, T366S, L368A, Y407V mutations in the other of the two CH3 domains or said trispecific or tetraspecific antibody comprises Y349C, T366W mutations in one of the two CH3 domains and S354C, T366S, L368A, Y407V mutations in the other of the two CH3 domains and additionally R409D; K370E mutations in the CH3 domain of the "knobs chain" and D399K; E357K mutations in the CH3 domain of the "hole chain".

The term "full length antibody" denotes an antibody consisting of two antibody heavy chains and two antibody light chains (see FIG. 1). A heavy chain of full length antibody is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in the case of an antibody of the subclass IgE. Preferably the heavy chain of full length antibody is a polypeptide consisting in N-terminal to C-terminal direction of VH, CH1, HR, CH2 and CH3. The light chain of full length antibody is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The full length antibody chains are linked together via inter-polypeptide disulfide bonds between the CL domain and the CH1 domain (i.e. between the light and heavy chain) and between the hinge regions of the full length antibody heavy chains. Examples of typical full length antibodies are natural antibodies like IgG (e.g. IgG1 and IgG2), IgM, IgA, IgD, and IgE.) The full length antibodies according to the invention can be from a single species e.g. human, or they can be chimerized or humanized antibodies. The full length antibodies according to the invention comprise two antigen binding sites each formed by a pair of VH and VL, which both specifically bind to the same antigen. The C-terminus of the heavy or light chain of said full length antibody denotes the last amino acid at the C-terminus of said heavy or light chain. The term "peptide connector" as used within the invention denotes a peptide with amino acid sequences, which is preferably of synthetic origin. These peptide connectors according to invention are used to fuse the antigen binding peptides to the C- or N-terminus of the full length and/or modified full length antibody chains to form a trispecific or tetraspecific antibody according to the invention. Preferably said peptide connectors under c) are peptides with an amino acid sequence with a length of at least 5 amino acids, preferably with a length of 5 to 100, more preferably of 10 to 50 amino acids. In one embodiment said peptide connector is (GxS)n or (GxS)nGm with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. In one embodiment said peptide connector is $(G_4S)_2$.

The term "antigen binding peptide" as used refers to a monovalent antigen binding fragment or derivative of a full length antibody which includes an antibody heavy chain variable domain (VH) and/or an antibody light chain variable domain (VL), or a pair of VH/VL derived from full length antibodies or antibody fragments such as a VH domain and/or a VL domain, a single chain Fv (scFv) fragment, or single chain Fab (scFab) fragment. Preferably the antigen binding peptide comprises at least an antibody heavy chain variable domain (VH) and an antibody light chain variable domain (VL). In a preferred embodiment the antigen binding peptides are selected from the group consisting of a VH domain, a single chain Fv (scFv) fragment, and a single chain Fab (scFab) fragment, preferably from the group consisting of a single chain Fv (scFv) fragment and a single chain Fab (scFab) fragment.

The terms "binding site" or "antigen-binding site" as used herein denotes the region(s) of an antibody to which a ligand (e.g., the antigen or antigen fragment) actually binds and is derived from an antibody. The antigen-binding site includes antibody heavy chain variable domains (VH) and/or an antibody light chain variable domains (VL), or pair of VH/VL.

The antigen-binding sites that specifically bind to the desired antigen can be derived from a) known antibodies to the antigen or b) new antibodies or antibody fragments obtained by de novo immunization methods using inter alia either the antigen protein or nucleic acid or fragments thereof or by phage display.

An antigen-binding site of an antibody of the invention can contain six complementarity determining regions (CDRs) which contribute in varying degrees to the affinity of the binding site for the antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences. Also included within the scope of the invention are functional antigen binding sites comprised of fewer CDRs (i.e., where binding specificity is determined by three, four or five CDRs). For example, less than a complete set of 6 CDRs may be sufficient for binding. In some cases, a VH or a VL domain will be sufficient.

Antibody specificity refers to selective recognition of the antibody for a particular epitope of an antigen. Natural antibodies, for example, are monospecific. Bispecific antibodies are antibodies which have two different antigen-binding specificities. Trispecific antibodies accordingly are antibodies of the invention which have three different antigen-binding specificities. Tetraspecific antibodies according to the invention are antibodies which have four different antigen-binding specificities.

Where an antibody has more than one specificity, the recognized epitopes may be associated with a single antigen or with more than one antigen.

The term "monospecific" antibody as used herein denotes an antibody that has one or more binding sites each of which bind to the same epitope of the same antigen.

The term "valent" as used within the current application denotes the presence of a specified number of binding sites in an antibody molecule. A natural antibody for example or a full length antibody according to the invention has two binding sites and is bivalent. As such, the term "trivalent", denotes the presence of three binding sites in an antibody molecule. The term "trivalent, trispecific" antibody as used herein denotes an antibody that has three antigen-binding sites of which each binds to another antigen (or another epitope of the antigen). Antibodies of the present invention have three to six binding sites, i.e. are tri-, tetra, penta-, or hexavalent (preferably tri or tetravalent) and are tri- or tetraspecific.

Figure 2A:
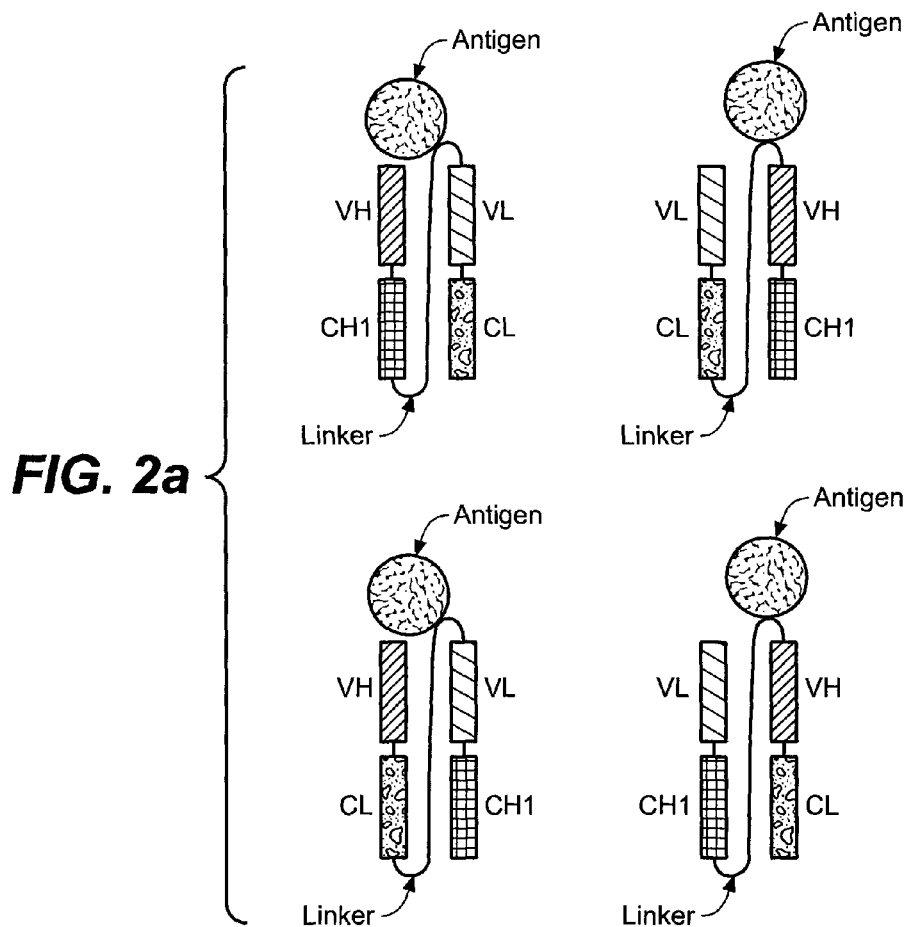
FIG. 2a Schematic structure of the four possible single chain Fab fragments specifically binding to an antigen FIG. 2b Schematic structure of the single chain Fv fragments specifically binding to an antigen FIG. 3a-d Schematic structure of different tri- or tetraspecific antibodies according to the invention characterized by the replacement of VL/VH domains and/or CL/CH1 domains in the full length antibody light/heavy chain of the antibody which specifically binds to the second antigen (without and with additional knobs into holes modifications of the CH3 domains)
Figure 2B:
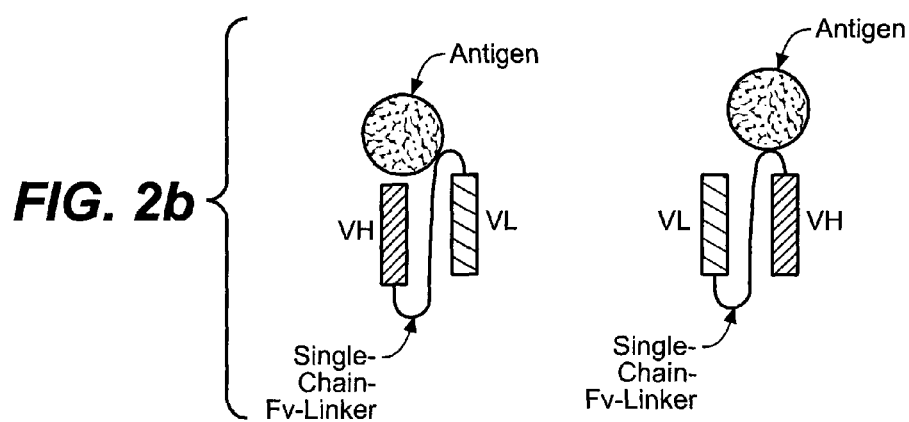
Figure 3B:
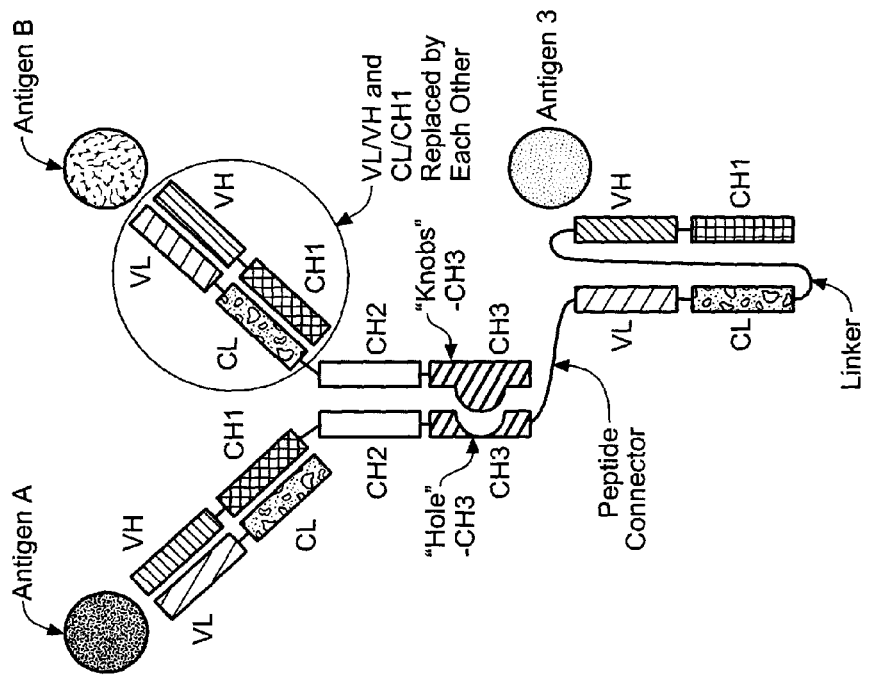
Figure 3A:
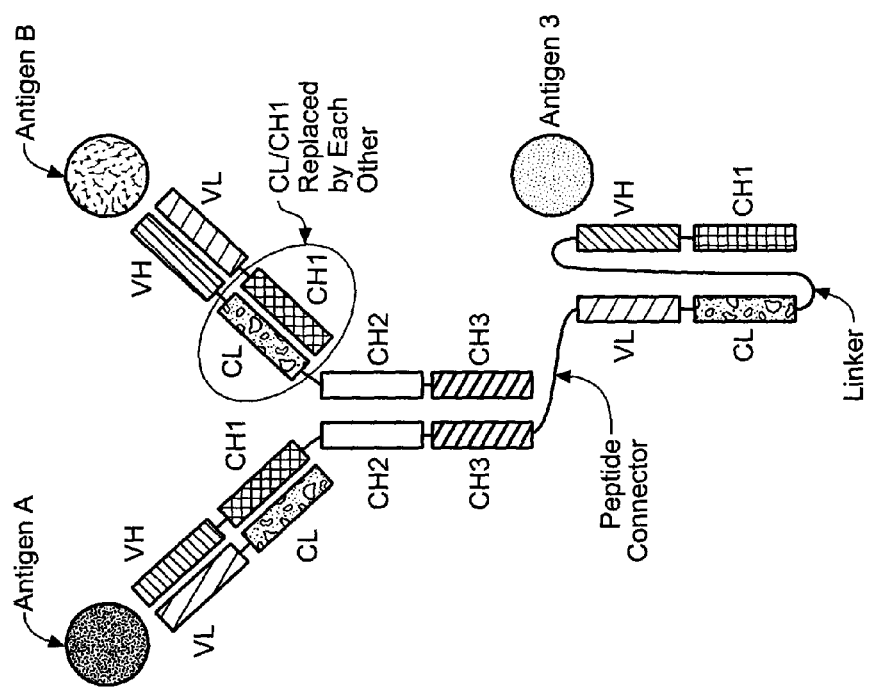
Figure 3D:
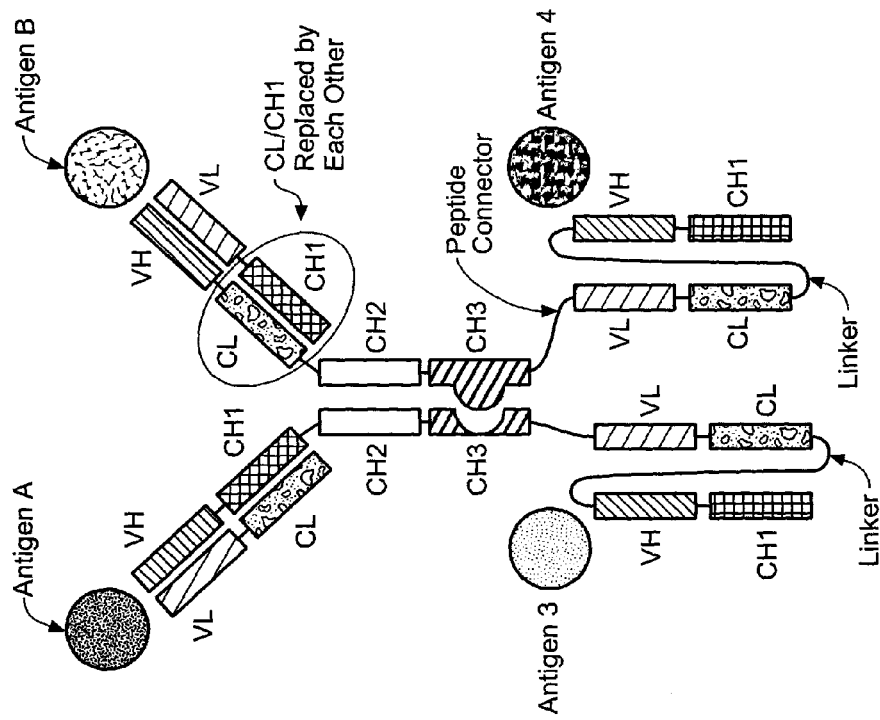
Figure 3C:
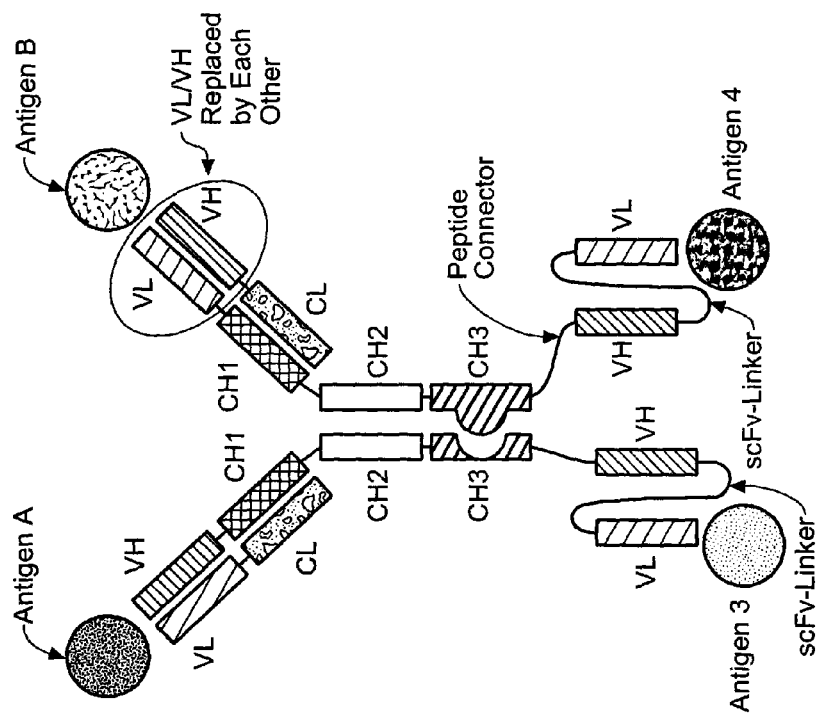

A "scFv fragment" or "single chain Fv fragment" (see FIG. 2b) is a polypeptide consisting of an antibody heavy chain variable domain (VH), an antibody light chain variable domain (VL), and a single-chain-Fv-linker, wherein said antibody domains and said single-chain-Fv-linker have one of the following orders in N-terminal to C-terminal direction: a) VH-single-chain-Fv-linker-VL, b) VL-single-chain-Fv-linker-VH; preferably a) VH-single-chain-Fv-linker-VL, and wherein said single-chain-Fv-linker is a polypeptide of with an amino acid sequence with a length of at least 15 amino acids, in one embodiment with a length of at least 20 amino acids. The term "N-terminus denotes the last amino acid of the N-terminus, The term "C-terminus denotes the last amino acid of the C-terminus.

The term "single-chain-Fv-linker" as used within single chain Fv fragment denotes a peptide with amino acid sequences, which is preferably of synthetic origin. Said single-chain-Fv-linker is a peptide with an amino acid sequence with a length of at least 15 amino acids, in one embodiment with a length of at least 20 amino acids and preferably with a length between 15 and 30 amino acids. In one embodiment said single-chain-linker is (GxS)n with G=glycine, S=serine, (x=3 and n=4, 5 or 6) or (x=4 and n=3, 4, 5 or 6), preferably with x=4, n=3, 4 or 5, more preferably with x=4, n=3 or 4. In one embodiment said single-chain-Fv-linker is $(G_4S)_3$ or $(G_4S)_4$.

Furthermore said single chain Fv fragments are preferably disulfide stabilized. Such further disulfide stabilization of single chain antibodies is achieved by the introduction of a disulfide bond between the variable domains of the single chain antibodies and is described e.g. in WO 94/029350, Rajagopal, V., et al., Prot. Engin. 10 (1997) 1453-59; Kobayashi, H., et al.; Nuclear Medicine & Biology, Vol. 25 (1998) 387-393; or Schmidt, M., et al., Oncogene 18 (1999) 1711-1721.

In one embodiment of the disulfide stabilized single chain Fv fragment, the disulfide bond between the variable domains of the single chain Fv fragments comprised in the antibody according to the invention is independently for each single chain Fv fragment selected from:

i) heavy chain variable domain position 44 to light chain variable domain position 100, ii) heavy chain variable domain position 105 to light chain variable domain position 43, or iii) heavy chain variable domain position 101 to light chain variable domain position 100.

In one embodiment the disulfide bond between the variable domains of the single chain Fv fragments comprised in the antibody according to the invention is between heavy chain variable domain position 44 and light chain variable domain position 100.

A "scFab fragment" or "single chain Fab fragment" (see FIG. 2a) is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments a) VH-CH1-linker-VL-CL, b) VL-CL-linker-VH-CH1, c) VH-CL-linker-VL-CH1 and d) VL-CH1-linker-VH-CL, are stabilized via the natural disulfide bond between the CL domain and the CH1 domain. The term "N-terminus denotes the last amino acid of the N-terminus, The term "C-terminus denotes the last amino acid of the C-terminus The term "linker" as used within the invention denotes a peptide with amino acid sequences, which is preferably of synthetic origin. These peptides according to invention are used to link a) VH-CH1 to VL-CL, b) VL-CL to VH-CH1, c) VH-CL to VL-CH1 or d) VL-CH1 to VH-CL to form the following single chain Fab fragments according to the invention a) VH-CH1-linker-VL-CL, b) VL-CL-linker-VH-CH1, c) VH-CL-linker-VL-CH1 or d) VL-CH1-linker-VH-CL. Said linker within the single chain Fab fragments is a peptide with an amino acid sequence with a length of at least 30 amino acids, preferably with a length of 32 to 50 amino acids. In one embodiment said linker is (GxS)n with G=glycine, S=serine, (x=3, n=8, 9 or 10 and m=0, 1, 2 or 3) or (x=4 and n=6, 7 or 8 and m=0, 1, 2 or 3), preferably with x=4, n=6 or 7 and m=0, 1, 2 or 3, more preferably with x=4, n=7 and m=2. In one embodiment said linker is $(G_4S)_6G_2$.

In a preferred embodiment said antibody domains and said linker in said single chain Fab fragment have one of the following orders in N-terminal to C-terminal direction:

a) VH-CH1-linker-VL-CL, or b) VL-CL-linker-VH-CH1, more preferably VL-CL-linker-VH-CH1.

In another preferred embodiment said antibody domains and said linker in said single chain Fab fragment have one of the following orders in N-terminal to C-terminal direction:
a) VH-CL-linker-VL-CH1 or b) VL-CH1-linker-VH-CL.

Optionally in said single chain Fab fragment, additionally to the natural disulfide bond between the CL-domain and the CH1 domain, also the antibody heavy chain variable domain (VH) and the antibody light chain variable domain (VL) are disulfide stabilized by introduction of a disulfide bond between the following positions:
i) heavy chain variable domain position 44 to light chain variable domain position 100,
ii) heavy chain variable domain position 105 to light chain variable domain position 43, or
iii) heavy chain variable domain position 101 to light chain variable domain position 100 (numbering always according to EU index of Kabat).

Such further disulfide stabilization of single chain Fab fragments is achieved by the introduction of a disulfide bond between the variable domains VH and VL of the single chain Fab fragments. Techniques to introduce unnatural disulfide bridges for stabilization of a single chain Fv are described e.g. in WO 94/029350, Rajagopal et al., Prot. Engin. 10 (1997) 1453-1459; Kobayashi et al., Nuclear Medicine & Biology 25 (1998) 387-393; or Schmidt et al., Oncogene 18 (1999) 1711-1721. In one embodiment the optional disulfide bond between the variable domains of the single chain Fab fragments comprised in the antibody according to the invention is between heavy chain variable domain position 44 and light chain variable domain position 100. In one embodiment the optional disulfide bond between the variable domains of the single chain Fab fragments comprised in the antibody according to the invention is between heavy chain variable domain position 105 and light chain variable domain position 43 (numbering always according to EU index of Kabat.

In an embodiment single chain Fab fragment without said optional disulfide stabilization between the variable domains VH and VL of the single chain Fab fragments are preferred.

The full length antibodies of the invention comprise immunoglobulin constant regions of one or more immunoglobulin classes. Immunoglobulin classes include IgG, IgM, IgA, IgD, and IgE isotypes and, in the case of IgG and IgA, their subtypes. In a preferred embodiment, a full length antibody of the invention has a constant domain structure of an IgG type antibody.

The terms "monoclonal antibody" or "monoclonal antibody composition" as used herein refer to a preparation of antibody molecules of a single amino acid composition. For clarity, the terms "monoclonal antibody" or "monoclonal antibody composition" are not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole, et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g., a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable domain of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and may form together with the CDRs from the other chain an antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, et al., Sequences of Proteins of Immunological Interest, 5th ed., Public Health Service, National Institutes of Health, Bethesda, Md. (1991).

As used herein, the terms "binding" or "which specifically binds" or "specifically binding" refer to the binding of the antibody to an epitope of the antigen in an in vitro assay, preferably in an plasmon resonance assay (BIAcore, GE-Healthcare Uppsala, Sweden) with purified wild-type antigen. The affinity of the binding is defined by the terms ka (rate constant for the association of the antibody from the antibody/antigen complex), $k_D$ (dissociation constant), and $K_D$ ($k_D$/ka). In one embodiment binding or specifically binding means a binding affinity ($K_D$) of $10^{-8}$ mol/l or less, preferably $10^{-9}$ M to $10^{-13}$ mol/l. Thus, an tri- or tetraspecific antibody according to the invention preferably specifically binds to each antigen for which it is specific with a binding affinity ($K_D$) of $10^{-8}$ mol/l or less, preferably $10^{-9}$ to $10^{-13}$ mol/l.

Binding of the antibody to the FcγRIII can be investigated by a BIAcore assay (GE-Healthcare Uppsala, Sweden). The affinity of the binding is defined by the terms ka (rate constant for the association of the antibody from the antibody/antigen complex), $k_D$ (dissociation constant), and $K_D$ ($k_D$/ka).

The term "epitope" includes any determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

In certain embodiments, an antibody is said to specifically bind an antigen when it preferentially recognizes its target antigen in a complex mixture of proteins and/or macromolecules.

In a further embodiment the tri- or tetraspecific antibody according to the invention is characterized in that said full length antibody is of human IgG1 subclass, or of human IgG1 subclass with the mutations L234A and L235A.

In a further embodiment the tri- or tetraspecific antibody according to the invention is characterized in that said full length antibody is of human IgG2 subclass.

In a further embodiment the tri- or tetraspecific antibody according to the invention is characterized in that said full length antibody is of human IgG3 subclass.

In a further embodiment the tri- or tetraspecific antibody according to the invention is characterized in that said full length antibody is of human IgG4 subclass or, of human IgG4 subclass with the additional mutation S228P.

Preferably the tri- or tetraspecific antibody according to the invention is characterized in that said full length antibody is of human IgG1 subclass, of human IgG4 subclass with the additional mutation S228P.

It has now been found that the tri- or tetraspecific antibodies according to the invention have improved characteristics such as biological or pharmacological activity, pharmacokinetic properties or toxicity. They can be used e.g. for the treatment of diseases such as cancer.

The term "constant region" as used within the current applications denotes the sum of the domains of an antibody other than the variable region. The constant region is not involved directly in binding of an antigen, but exhibit various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions (CL) which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the art and e.g. described by Kabat, E. A., (see e.g. Johnson, G. and Wu, T. T., Nucleic Acids Res. 28 (2000) 214-218; Kabat, E. A., et al., Proc. Natl. Acad. Sci. USA 72 (1975) 2785-2788).

While antibodies of the IgG4 subclass show reduced Fc receptor (FcγRIIIa) binding, antibodies of other IgG subclasses show strong binding. However, Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antibody according to the invention has a reduced FcR binding compared to an IgG1 antibody. Thus, the full length parent antibody is in regard to FcR binding of IgG4 subclass or of IgG1 or IgG2 subclass with a mutation in S228, L234, L235 and/or D265, and/or contains the PVA236 mutation. In one embodiment the mutations in the full length parent antibody are S228P, L234A, L235A, L235E and/or PVA236. In another embodiment the mutations in the full length parent antibody are in IgG4 S228P and in IgG1 L234A and L235A.

The constant region of an antibody is directly involved in ADCC (antibody-dependent cell-mediated cytotoxicity) and CDC (complement-dependent cytotoxicity). Complement activation (CDC) is initiated by binding of complement factor C1q to the constant region of most IgG antibody subclasses. Binding of C1q to an antibody is caused by defined protein-protein interactions at the so called binding site. Such constant region binding sites are known in the art and described e.g. by Lukas, T. J., et al., J. Immunol. 127 (1981) 2555-2560; Bunkhouse, R. and Cobra, J. J., Mol. Immunol. 16 (1979) 907-917; Burton, D. R., et al., Nature 288 (1980) 338-344; Thomason, J. E., et al., Mol. Immunol. 37 (2000) 995-1004; Idiocies, E. E., et al., J. Immunol. 164 (2000) 4178-4184; Hearer, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat).

The term "antibody-dependent cellular cytotoxicity (ADCC)" refers to lysis of human target cells by an antibody according to the invention in the presence of effector cells. ADCC is measured preferably by the treatment of a preparation of antigen expressing cells with an antibody according to the invention in the presence of effector cells such as freshly isolated PBMC or purified effector cells from buffy coats, like monocytes or natural killer (NK) cells or a permanently growing NK cell line.

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

Cell-mediated effector functions of monoclonal antibodies can be enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M., R., et al., Glycobiology 5 (1995) 813-822; Jefferis, R., et al., Immunol. Rev. 163 (1998) 59-76; Wright, A., and Morrison, S. L., Trends Biotechnol. 15 (1997) 26-32). Umana, P., et al., Nature Biotechnol. 17 (1999) 176-180 and WO 99/54342 showed that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R. L., et al., J. Biol. Chem. 276 (2001) 6591-6604; Shields, R. L., et al., J. Biol. Chem. 277 (2002) 26733-26740; Simmons, L. C., et al., J. Immunol. Methods 263 (2002) 133-147).

Methods to enhance cell-mediated effector functions of monoclonal antibodies are reported e.g. in WO 2005/018572, WO 2006/116260, WO 2006/114700, WO 2004/065540, WO 2005/011735, WO 2005/027966, WO 1997/028267, US 2006/0134709, US 2005/0054048, US 2005/0152894, WO 2003/035835, WO 2000/061739.

In one preferred embodiment of the invention, the tri- or tetraspecific antibody is glycosylated (if it comprises an Fc part of IgG1, IgG2, IgG3 or IgG4 subclass, preferably of IgG1 or IgG3 subclass) with a sugar chain at Asn297 whereby the amount of fucose within said sugar chain is 65% or lower (Numbering according to Kabat). In another embodiment the amount of fucose within said sugar chain is between 5% and 65%, preferably between 20% and 40%. "Asn297" according to the invention means amino acid asparagine located at about position 297 in the Fc region. Based on minor sequence variations of antibodies, Asn297 can also be located some amino acids (usually not more than ±3 amino acids) upstream or downstream of position 297, i.e. between position 294 and 300. In one embodiment the glycosylated antibody according to the invention the IgG subclass is of human IgG1 subclass, of human IgG1 subclass with the mutations L234A and L235A or of IgG3 subclass. In a further embodiment the amount of N-glycolylneuraminic acid (NGNA) is 1% or less and/or the amount of N-terminal alpha-1,3-galactose is 1% or less within said sugar chain. The sugar chain show preferably the characteristics of N-linked glycans attached to Asn297 of an antibody recombinantly expressed in a CHO cell.

The term "the sugar chains show characteristics of N-linked glycans attached to Asn297 of an antibody recombinantly expressed in a CHO cell" denotes that the sugar chain at Asn297 of the full length parent antibody according to the invention has the same structure and sugar residue sequence except for the fucose residue as those of the same antibody expressed in unmodified CHO cells, e.g., as those reported in WO 2006/103100.

The term "NGNA" as used within this application denotes the sugar residue N-glycolylneuraminic acid.

Glycosylation of human IgG1 or IgG3 occurs at Asn297 as core fucosylated biantennary complex oligosaccharide glycosylation terminated with up to two Gal residues. Human constant heavy chain regions of the IgG1 or IgG3 subclass are reported in detail by Kabat, E., A., et al., Sequences of Proteins of Immunological Interest, 5th Ed. Public Health Service, National Institutes of Health, Bethesda, Md. (1991), and by Bruggemann, M., et al., J. Exp. Med. 166 (1987) 1351-1361; Love, T., W., et al., Methods Enzymol. 178 (1989) 515-527. These structures are designated as G0, G1 (α-1,6- or α-1,3-), or G2 glycan residues, depending from the amount of terminal Gal residues (Raju, T., S., Bioprocess Int. 1 (2003) 44-53). CHO type glycosylation of antibody Fc parts is e.g. described by Routier, F., H., Glycoconjugate J. 14 (1997) 201-207. Antibodies which are recombinantly expressed in non-glycomodified CHO host cells usually are fucosylated at Asn297 in an amount of at least 85%. The modified oligosaccharides of the full length parent antibody may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of said sugar within the sugar chain at Asn297, related to the sum of all glycostructures attached to Asn297 (e.g., complex, hybrid and high mannose structures) measured by MALDI-TOF mass spectrometry and calculated as average value. The relative amount of fucose is the percentage of fucose-containing structures related to all glycostructures identified in an N-Glycosidase F treated sample (e.g. complex, hybrid and oligo- and high-mannose structures, resp.) by MALDI-TOF.

The antibody according to the invention is produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (supernatant or cells after lysis). General methods for recombinant production of antibodies are well-known in the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The tri- or tetraspecific antibodies according to the invention are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the tri- or tetraspecific antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous Linking is accomplished by ligation at convenient restriction sites. If such sites do not exist, the synthetic oligonucleotide adaptors or linkers are used in accordance with conventional practice.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and in widespread use for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g., a pharmaceutical composition, containing an antibody according to the present invention, formulated together with a pharmaceutical carrier.

One embodiment of the invention is the tri- or tetraspecific antibody according to the invention for the treatment of cancer.

Another aspect of the invention is said pharmaceutical composition for the treatment of cancer.

Another aspect of the invention is the use of an antibody according to the invention for the manufacture of a medicament for the treatment of cancer.

Another aspect of the invention is method of treatment of patient suffering from cancer by administering an antibody according to the invention to a patient in need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term "cancer" as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 (1978) 546ff. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, F. N, et al, PNAS. 69 (1972) 7110ff.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The following examples, sequence listing and figures are provided to aid the understanding of the present invention, the true scope of which is set forth in the appended claims. It is understood that modifications can be made in the procedures set forth without departing from the spirit of the invention.

Description of the Amino Acid Sequences

SEQ ID NO:1 light chain <Ang-2>

SEQ ID NO:2 knobs-heavy chain <Ang-2> with C-terminal fused <EGFR> scFv

SEQ ID NO:3 light chain <VEGF> with CH1-CL exchange

SEQ ID NO:4 holes-heavy chain <VEGF> with CH1-CL exchange and C-terminal fused <IGF-1R> scFv SEQ ID NO:5 knobs-heavy chain <Ang-2> with C-terminal fused <EGFR> scFab SEQ ID NO:6 holes-heavy chain <VEGF> with CH1-CL exchange and C-terminal fused <IGF-1R> scFab SEQ ID NO:7 holes-heavy chain <VEGF> with CH1-CL exchange and C-terminal fused <EGFR> scFv SEQ ID NO:8 holes-heavy chain <VEGF> with CH1-CL exchange SEQ ID NO:9 holes-heavy chain <VEGF> with CH1-CL exchange and C-terminal fused <EGFR> scFab SEQ ID NO:10 knobs-heavy chain <Ang-2> with C-terminal fused <IGF-1R> scFab

EXAMPLES

Materials & General Methods

General information regarding the nucleotide sequences of human immunoglobulin light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md., (1991)).

Recombinant DNA Techniques

Standard methods were used to manipulate DNA as described in Sambrook, J. et al., Molecular Cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The 600-1800 bp long gene segments, which were flanked by singular restriction endonuclease cleavage sites, were assembled by annealing and ligating oligonucleotides including PCR amplification and subsequently cloned via the indicated restriction sites e.g. KpnI/SacI or AscI/PacI into a pPCRScript (Stratagene) based pGA4 cloning vector. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors

For the expression of the described antibodies, variants of expression plasmids for transient expression (e.g. in HEK293 EBNA or HEK293-F) cells based either on a cDNA organization with or without a CMV-Intron A promoter or on a genomic organization with a CMV promoter were applied.

Beside the antibody expression cassette the vectors contained:

an origin of replication which allows replication of this plasmid in E. coli, and a β-lactamase gene which confers ampicillin resistance in E. coli.

The transcription unit of the antibody gene was composed of the following elements:

unique restriction site(s) at the 5' end the immediate early enhancer and promoter from the human cytomegalovirus, followed by the Intron A sequence in the case of the cDNA organization, a 5'-untranslated region of a human antibody gene, an immunoglobulin heavy chain signal sequence, the human antibody chain (wildtype or with domain exchange) either as cDNA or as genomic organization with the immunoglobulin exon-intron organization a 3' untranslated region with a polyadenylation signal sequence, and unique restriction site(s) at the 3' end.

The fusion genes comprising the antibody chains as described below were generated by PCR and/or gene synthesis and assembled by known recombinant methods and techniques by connection of the according nucleic acid segments e.g. using unique restriction sites in the respective vectors. The subcloned nucleic acid sequences were verified by DNA sequencing. For transient transfections larger quantities of the plasmids were prepared by plasmid preparation from transformed E. coli cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Tri- or tetraspecific antibodies were expressed by transient co-transfection of the respective expression plasmids in adherently growing HEK293-EBNA or in HEK29-F cells growing in suspension as described below.

Transient Transfections in HEK293-EBNA System

Tri- or tetraspecific antibodies were expressed by transient co-transfection of the respective expression plasmids (e.g. encoding the heavy and modified heavy chain, as well as the corresponding light and modified light chain) in adherently growing HEK293-EBNA cells (human embryonic kidney cell line 293 expressing Epstein-Barr-Virus nuclear antigen; American type culture collection deposit number ATCC #CRL-10852, Lot. 959 218) cultivated in DMEM (Dulbecco's modified Eagle's medium, Gibco®) supplemented with 10% Ultra Low IgG FCS (fetal calf serum, Gibco®), 2 mM L-Glutamine (Gibco®), and 250 µg/ml Geneticin (Gibco®). For transfection FuGENE™ 6 Transfection Reagent (Roche Molecular Biochemicals) was used in a ratio of FuGENE™ reagent (µl) to DNA (µg) of 4:1 (ranging from 3:1 to 6:1). Proteins were expressed from the respective plasmids using a molar ratio of (modified and wildtype) light chain and heavy chain encoding plasmids of 1:1 (equimolar) ranging from 1:2 to 2:1, respectively. Cells were fed at day 3 with L-Glutamine ad 4 mM, Glucose [Sigma] and NAA [Gibco®]. Tri- or tetraspecific antibody containing cell culture supernatants were harvested from day 5 to 11 after transfection by centrifugation and stored at −20° C. General information regarding the recombinant expression of human immunoglobulins in e.g. HEK293 cells is given in: Meissner, P. et al., Biotechnol. Bioeng. 75 (2001) 197-203.

Transient Transfections in HEK293-F System

Tri- or tetraspecific antibodies were generated by transient transfection with the respective plasmids (e.g. encoding the heavy and modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with a mix of the four expression plasmids and 293fectin™ or fectin (Invitrogen). For 2 L shake flask (Corning) HEK293-F cells were seeded at a density of 1.0E*6 cells/mL in 600 mL and incubated at 120 rpm, 8% CO2. The day after the cells were transfected at a cell density of ca. 1.5E*6 cells/mL with ca. 42 mL mix of A) 20 mL Opti-MEM (Invitrogen) with 600 µg total plasmid DNA (1 µg/mL) encoding the heavy or modified heavy chain, respectively and the corresponding light chain in an equimolar ratio and B) 20 ml Opti-MEM+1.2 mL 293 fectin or fectin (2 µl/mL). According to the glucose consumption glucose solution was added during the course of the fermentation. The supernatant containing the secreted antibody was harvested after 5-10 days and antibodies were either directly purified from the supernatant or the supernatant was frozen and stored.

Protein Determination

The protein concentration of purified antibodies and derivatives was determined by determining the optical density (OD) at 280 nm, using the molar extinction coefficient calculated on the basis of the amino acid sequence according to Pace, et al., Protein Science, 1995, 4, 2411-1423.

Antibody Concentration Determination in Supernatants

The concentration of antibodies and derivatives in cell culture supernatants was estimated by immunoprecipitation with Protein A Agarose-beads (Roche). 60 µL Protein A Agarose beads were washed three times in TBS-NP40 (50 mM Tris, pH 7.5, 150 mM NaCl, 1% Nonidet-P40). Subsequently, 1-15 mL cell culture supernatant were applied to the Protein A Agarose beads pre-equilibrated in TBS-NP40. After incubation for at 1 hour at room temperature the beads were washed on an Ultrafree-MC-filter column (Amicon) once with 0.5 mL TBS-NP40, twice with 0.5 mL 2× phosphate buffered saline (2×PBS, Roche) and briefly four times with 0.5 mL 100 mM Na-citrate pH 5.0. Bound antibody was eluted by addition of 35 µl NuPAGE® LDS Sample Buffer (Invitrogen). Half of the sample was combined with NuPAGE® Sample Reducing Agent or left unreduced, respectively, and heated for 10 min at 70° C. Consequently, 5-30 µl were applied to a 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of antibodies and derivatives in cell culture supernatants was quantitatively measured by affinity HPLC chromatography. Briefly, cell culture supernatants containing antibodies and derivatives that bind to Protein A were applied to an Applied Biosystems Poros A/20 column in 200 mM KH2PO4, 100 mM sodium citrate, pH 7.4 and eluted from the matrix with 200 mM NaCl, 100 mM citric acid, pH 2.5 on an Agilent HPLC 1100 system. The eluted protein was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Strepatavidin A-96 well microtiter plates (Roche) are coated with 100 µl/well biotinylated anti-human IgG capture molecule F(ab')2<h-Fcγ> BI (Dianova) at 0.1 µg/mL for 1 hour at room temperature or alternatively overnight at 4° C. and subsequently washed three times with 200 µL/well PBS, 0.05% Tween (PBST, Sigma). 100 µL/well of a dilution series in PBS (Sigma) of the respective antibody containing cell culture supernatants was added to the wells and incubated for 1-2 hour on a microtiterplate shaker at room temperature. The wells were washed three times with 200 µL/well PBST and bound antibody was detected with 100 µl F(ab')2<hFcγ>POD (Dianova) at 0.1 µg/mL as the detection antibody for 1-2 hours on a microtiterplate shaker at room temperature. Unbound detection antibody was washed away three times with 200 µL/well PBST and the bound detection antibody was detected by addition of 100 µL ABTS/well. Determination of absorbance was performed on a Tecan Fluor Spectrometer at a measurement wavelength of 405 nm (reference wavelength 492 nm).

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSK gel G3000SW column in 300 mM NaCl, 50 mM KH2PO4/K2HPO4, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

The total deglycosylated mass of crossover antibodies was determined and confirmed via electrospray ionization mass spectrometry (ESI-MS). Briefly, 100 µg purified antibodies were deglycosylated with 50 mU N-Glycosidase F (PNGaseF, ProZyme) in 100 mM KH2PO4/K2HPO4, pH 7 at 37° C. for 12-24 h at a protein concentration of up to 2 mg/ml and subsequently desalted via HPLC on a Sephadex G25 column (GE Healthcare). The mass of the respective heavy and light chains was determined by ESI-MS after deglycosylation and reduction. In brief, 50 µg antibody in 115 µl were incubated with 60 µl 1M TCEP and 50 µl 8 M Guanidine-hydrochloride and subsequently desalted. The total mass and the mass of the reduced heavy and light chains was determined via ESI-MS on a Q-Star Elite MS system equipped with a NanoMate® source.

IGF-1R, EGFR, HER3 and c-Met ECD Biacore

Figure 11:
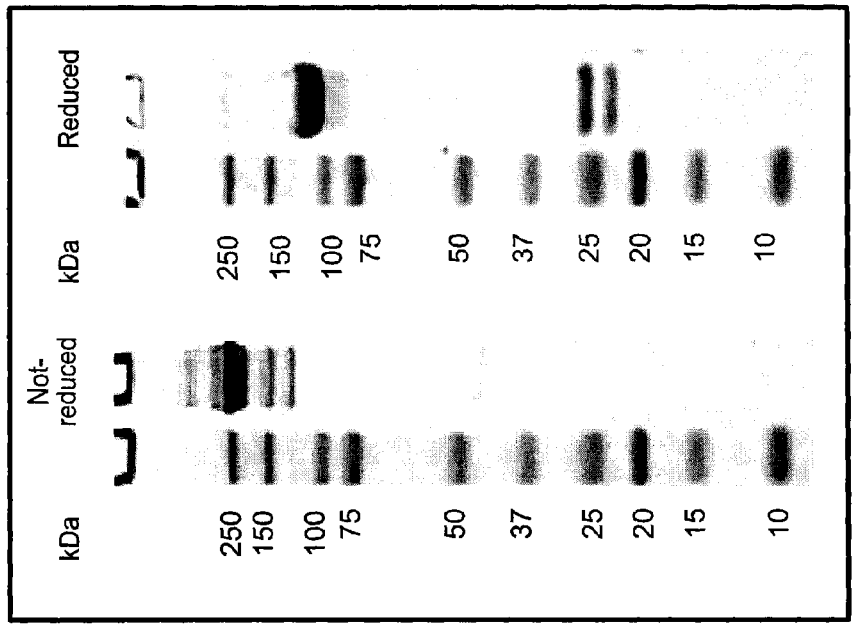
FIG. 11 SDS-PAGE analysis of a trispecific antibody according to the invention recognizing Angiopoietin-2, VEGF-A and EGFR, which is tetravalent and uses single chain Fab fragments as antigen binding peptides (Example 2) under native and denaturing conditions.

Binding of the generated antibodies to human IGF-1R, EGFR, HER3 and c-Met ECDs (Extracellular Domains) was investigated by surface plasmon resonance using a BIACORE T100 instrument (GE Healthcare Biosciences AB, Uppsala, Sweden). Briefly, for affinity measurements Goat-Anti-Human IgG, JIR 109-005-098 antibodies were immobilized on a CM5 chip via amine coupling for presentation of the antibodies against human ECD-Fc tagged. Binding was measured in HBS buffer (HBS-P (10 mM HEPES, 150 mM NaCl, 0.005% Tween 20, ph 7.4), 25° C. ECD from c-Met, IGF-1R or EGFR (R&D Systems or in house purified) was added in various concentrations in solution. Association was measured by an ECD injection of 80 seconds to 3 minutes; dissociation was measured by washing the chip surface with HBS buffer for 3-10 minutes and a KD value was estimated using a 1:1 Langmuir binding model. Due to low loading density and capturing level monovalent ECD binding was obtained. Negative control data (e.g. buffer curves) were subtracted from sample curves for correction of system intrinsic baseline drift and for noise signal reduction. Biacore T100 Evaluation Software version 1.1.1 was used for analysis of sensorgrams and for calculation of affinity data. FIG. 11 shows a scheme of the Biacore assay.

ANGPT2 and VEGF Binding BIACORE

Binding of the generated antibodies to human ANGPT2 and VEGF was also investigated by surface plasmon resonance using a BIACORE T100 instrument (GE Healthcare Biosciences AB, Uppsala, Sweden). Briefly, for affinity measurements goat<hIgG-Fcg> polyclonal antibodies were immobilized on a CM5 or CM4 chip via amine coupling for presentation of the antibodies against human ANGPT2 and VEGF. Binding was measured in HBS buffer (HBS-P (10 mM HEPES, 150 mM NaCl, 0.005% Tween 20, ph 7.4) with or without 5 mM Ca2+, 25° C. Purified ANGPT2-His or VEGF165/VEGF121-His respectively (R&D Systems or in house purified) was added in various concentrations in solution. Association was measured by an ANGPT2/VEGF-injection of 3 minutes; dissociation was measured by washing the chip surface with HBS buffer for 3 to 5 minutes and a KD value was estimated using a 1:1 Langmuir binding model. Negative control data (e.g. buffer curves) were subtracted from sample curves for correction of system intrinsic baseline drift and for noise signal reduction. Biacore T100 Evaluation Software version 1.1.1 was used for analysis of sensorgrams and for calculation of affinity data.

Simultaneous Binding in BIACORE

Simultaneous binding of tetra- and trispecific antibodies to EGFR, IGF-1R, Ang-2 and VEGF or EGFR, IGF-1R, HER3 and c-Met or EGFR, Ang-2 and VEGF, respectively.

The binding of the tetra- or trispecific antibody formats was compared to the binding of the 'wildtype' IgGs from which the binding modules and bispecific antibodies were derived. These analyses were carried out by applying Surface Plasmon Resonance (Biacore), as described above. In order to show simultaneous binding the binding properties were analyzed by surface plasmon resonance (SPR) technology using a Biacore T100 instrument (Biacore AB, Uppsala).

Capturing anti-human IgG antibody was immobilized on the surface of a CM5 biosensorchip using amine-coupling chemistry. Flow cells were activated with a 1:1 mixture of 0.1 M N-hydroxysuccinimide and 0.1 M 3-(N,N-dimethylamino)propyl-N-ethylcarbodiimide at a flow rate of 5 µl/min. Anti-human IgG antibody was injected in sodium acetate, pH 5.0 at 10 µg/ml, which results in a surface density of approximately 12000 RU. A reference control flow cell was treated in the same way but with vehicle buffers only instead of the capturing antibody. Surfaces were blocked with an injection of 1 M ethanolamine/HCl, pH 8.5. The multispecific antibodies were diluted in HBS-P and injected at a flow rate of 5 µl/min. The contact time (association phase) was 1 min for the antibodies at a concentration between 1 and 50 nM. EGFR/IGF-1R/HER3/c-Met-ECD and Ang-2 or VEGF respectively were injected at increasing concentrations. All interactions were performed at 25° C. (standard temperature). The regeneration solution of 3 M Magnesium chloride was injected for 60 sec at 5 µl/min flow to remove any non-covalently bound protein after each binding cycle. Signals were detected at a rate of one signal per second. Samples were injected at increasing concentrations.

Example 1

Figure 4B:
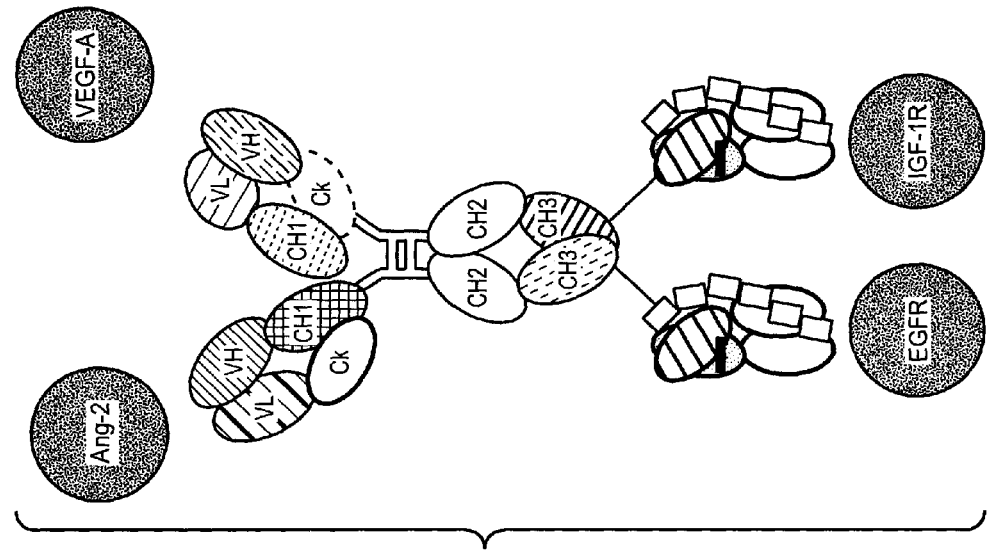
FIG. 4b Schematic structure of a tetraspecific antibody according to the invention recognizing Angiopoietin-2, VEGF-A, EGFR and IGF-1R, which is tetravalent and uses single chain Fab fragments as antigen binding peptides (Example 1)
Figure 4A:
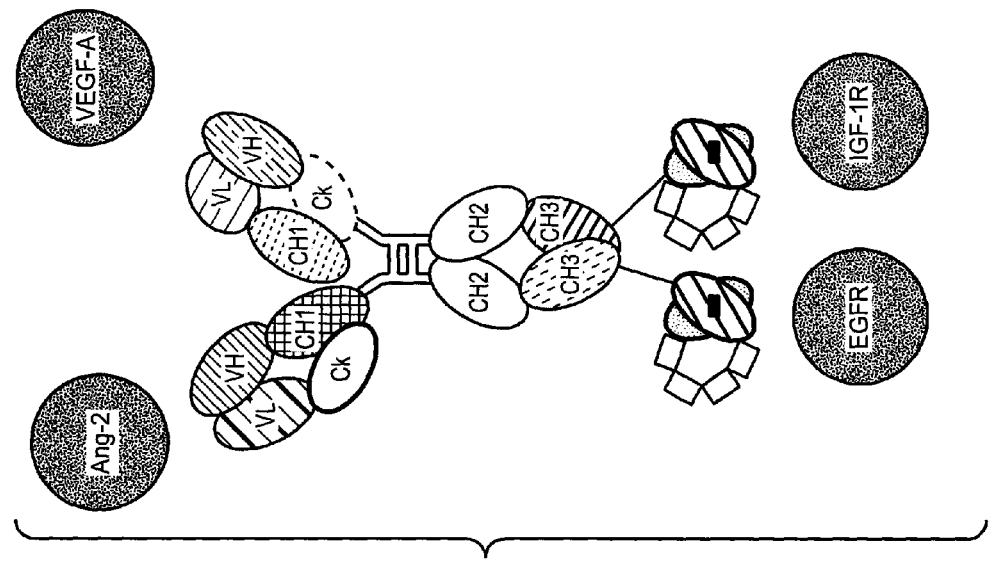
FIG. 4a Schematic structure of a tetraspecific antibody according to the invention recognizing Angiopoietin-2, VEGF-A, EGFR and IGF-1R, which is tetravalent and uses disulfide stabilized single chain Fv fragments as antigen binding peptides (Example 1)
Figure 7:
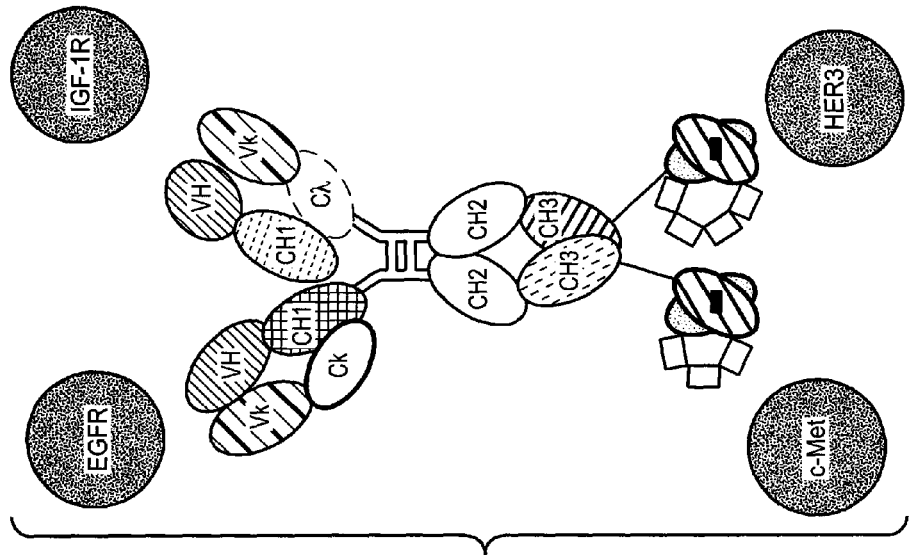
FIG. 7 Schematic structure of a tetraspecific antibody according to the invention recognizing EGFR, IGF-1R, c-Met and HER3 which is tetravalent and uses disulfide stabilized single chain Fv fragments as antigen binding peptides FIG. 8 Size Exclusion Chromatography of a tetraspecific antibody according to the invention recognizing Angiopoietin-2, VEGF-A, EGFR and IGF-1R, which is tetravalent and uses single chain Fab fragments as antigen binding peptides (Example 1) on a high load 26/60 Superdex 200 column.

Production, Expression, Purification and Characterization of a Tetraspecific and Tetravalent Antibody Recognizing Angiopoietin-2, VEGF-A, EGFR and IGF-1R In a first example, a tetraspecific and tetravalent antibody recognizing Angiopoietin-2, VEGF-A, EGFR and IGF-1R was made by fusing via a (G4S)4-connector a disulfide stabilized scFv against EGFR to the C-terminus part of the first heavy chain and a scFv against IGF-1R to the C-terminus of the second heavy chain of a CH1/CL(Ckappa) domain exchanged antibody with knobs-into-holes recognizing Angiopoietin-2 and VEGF with its variable domains (FIG. 4*a*). The sequences of the respective 4 antibody chains are given in SEQ ID NO:1, SEQ ID NO:2, SEQ ID NO:3 and SEQ ID NO:4.

| Key Data | |
|---|---|
| Expression (Yield) - mg/mL | 14.5 |
| Purification (Prot. A homogeneity) - % | 91.3 |
| Yield after SEC - mg/mL | 10.4 |
| Homogeneity after preparative SEC - % | 99.7 |

In a second example a tetraspecific and tetravalent antibody recognizing Angiopoietin-2, VEGF-A, EGFR and IGF-1R was made by fusing via a (G4S)2-connector a scFab against EGFR to the C-terminus part of the first heavy chain and a scFab against IGF-1R to the C-terminus of the second heavy chain of a CH1/CL (Ckappa) domain exchanged antibody with knobs-into-holes recognizing Angiopoietin-2 and VEGF with its variable domains (FIG. 4b). The sequences of the respective 4 antibody chains are given in SEQ ID NO:1, SEQ ID NO:5, SEQ ID NO:3 and SEQ ID NO:6.

| Key Data | |
|---|---|
| Expression (Yield) - mg/mL | 12.2 |
| Purification (Prot. A homogeneity) - % | 74.4 |
| Yield after SEC - mg/mL | 6.8 |
| Homogeneity after preparative SEC - % | 98.4 |

In further example analogous to the second example a tetraspecific and tetravalent antibody recognizing Angiopoietin-2, VEGF-A, EGFR and IGF-1R was made by fusing via a (G4S)2-connector a scFab against EGFR to the C-terminus part of the second heavy chain and a scFab against IGF-1R to the C-terminus of the first heavy chain of a CH1/CL (Ckappa) domain exchanged antibody with knobs-into-holes recognizing Angiopoietin-2 and VEGF with its variable domains (analogous to FIG. 4b, but with a scFab against IGF-1R fused to the knobs ANG2 binding heavy chain and a scFab against EGFR fused to the holes-VEGF binding heavy chain). The sequences of the respective 4 antibody chains are given in SEQ ID NO:1, SEQ ID NO:3, SEQ ID NO:9 and SEQ ID NO:10.

Figure 8:
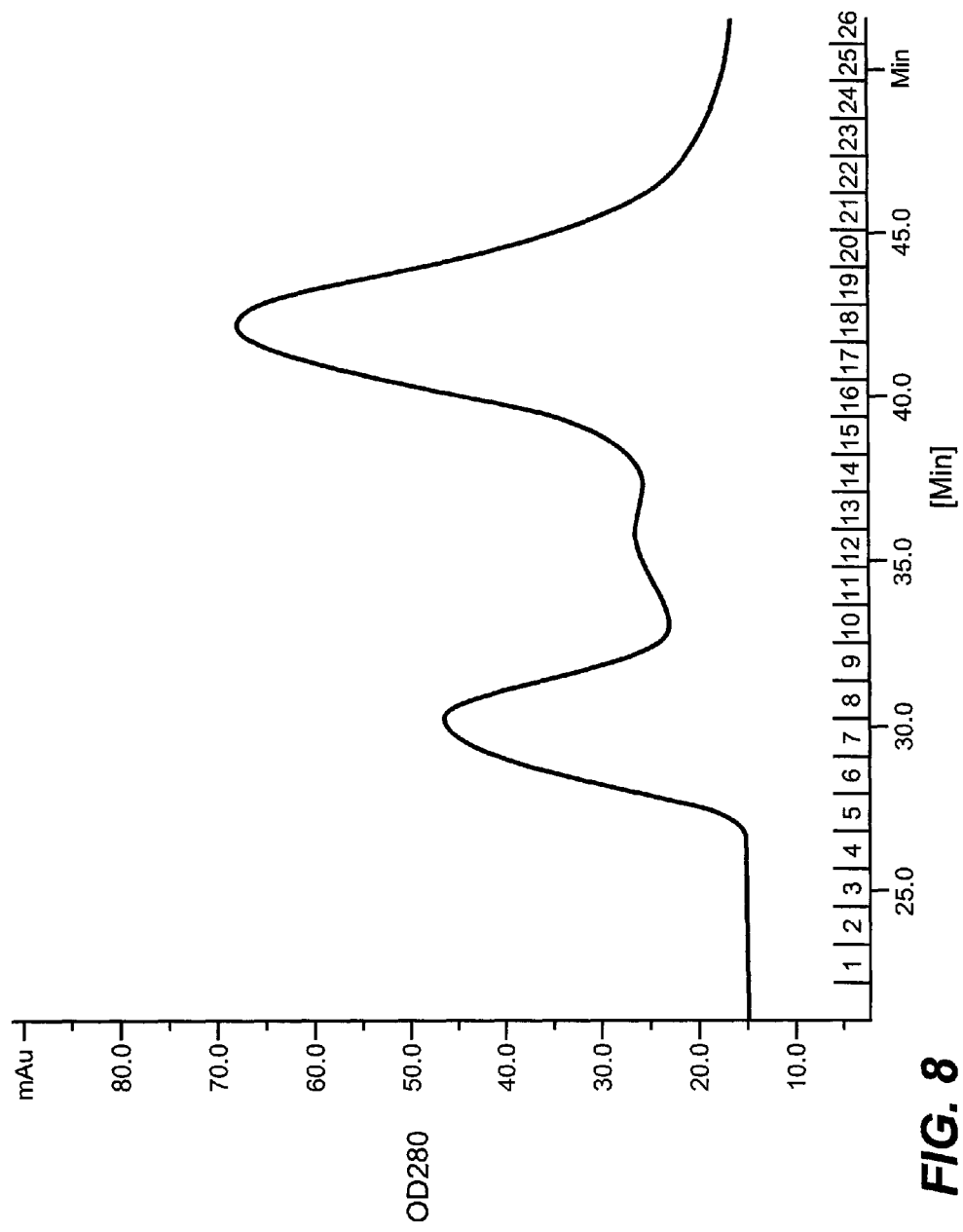
Figure 9:
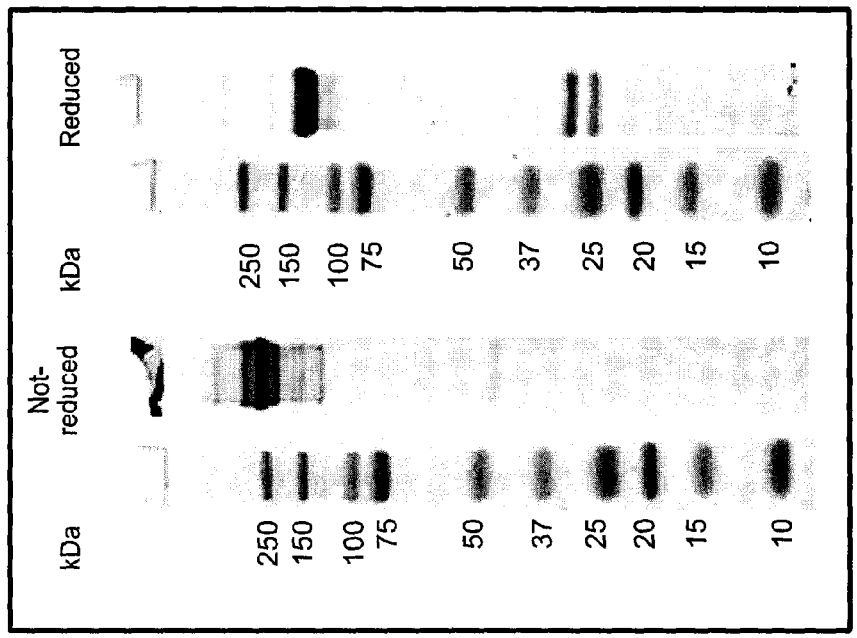
FIG. 9 SDS-PAGE analysis of a tetraspecific antibody according to the invention recognizing Angiopoietin-2, VEGF-A, EGFR and IGF-1R, which is tetravalent and uses single chain Fab fragments as antigen binding peptides (Example 1) under native and denaturing conditions.

These antibody variants were generated as described above in the general methods section by classical molecular biology techniques and were expressed transiently in HEK293F cells as described above. Subsequently, they are purified from the supernatant by a combination of Protein A affinity chromatography and size exclusion chromatography. The obtained products were characterized for identity by mass spectrometry and analytical properties such as purity by SDS-PAGE, monomer content and stability (FIGS. 8-9, based on SEQ ID NO:1, SEQ ID NO:3, SEQ ID NO:9 and SEQ ID NO:10).

(Simultaneous) binding of the four antibody specificities to the four covered antigens (Angiopoietin-2, VEGF-A, EGFR and IGF-1R) was shown by Biacore using the methods described above.

TABLE

Binding of tetraspecific and tetravalent antibody recognizing Angiopoietin-2, VEGF-A, EGFR and IGF-1R based on SEQ ID NO: 1, SEQ ID NO: 3, SEQ ID NO: 9 and SEQ ID NO: 10).

| Analyte | ka (1/Ms) | kd (1/s) | KD (nM) |
|---|---|---|---|
| EGFR (HER1) | 3.1E+05* | 3.9E−05* | 12.8* |
| IGF-1R | | | Low binding affinity |
| Ang-2 | n.d.*** | n.d.*** | 138*** |
| VEGF | 5.0E+04* | <1E−06* | <1E−11* |

*Capturing via anti-human antibody
**Capturing via HER1
***Ang-2 surface

Example 2

Production, Expression, Purification and Characterization of a Trispecific and Tetravalent Antibody Recognizing Angiopoietin-2, VEGF-A and EGFR In a first example, a trispecific and tetravalent antibody recognizing Angiopoietin-2, VEGF-A, EGFR and IGF-1R was made by fusing via a (G4S)4-connector a disulfide stabilized scFv against EGFR to the C-termini part of the two heavy chains of a CH1/CL(Ckappa) domain exchanged antibody with knobs-into-holes recognizing Angiopoietin-2 and VEGF with its variable domains (FIG. 5a). The sequences of the respective 4 antibody chains are given in SEQ ID NO:1, SEQ ID NO:2, SEQ ID NO:3 and SEQ ID NO:7.

| Key Data | |
|---|---|
| Expression (Yield) - mg/mL | 20.1 |
| Purification (Prot. A homogeneity) - % | 64.1 |
| Yield after SEC - mg/mL | 12.0 |
| Homogeneity after preparative SEC - % | 100 |

TABLE

Binding of trispecific and tetravalent antibody recognizing Angiopoietin-2, VEGF-A, and EGFR according to FIG. 5a.

| Binding affiinity to | ka (1/Ms) | kd (1/s) | KD (nM) |
|---|---|---|---|
| EGFR (HER1) | 4.7E+04 | 2.3E−04 | 6 |
| hAng-2 | 1E+06 | 1.7E−04 | 0.2 |
| hVEGF | 1E+05 | <1E−06 | <0.1 |

In a second example, a trispecific and tetravalent antibody recognizing Angiopoietin-2, VEGF-A, EGFR and IGF-1R was made by fusing via a (G4S)2-connector two scFab against EGFR to the C-termini part of the two heavy chains of a CH1/CL(Ckappa) domain exchanged antibody with knobs-into-holes recognizing Angiopoietin-2 and VEGF with its variable domains (FIG. 5b). The sequences of the respective 4 antibody chains are given in SEQ ID NO:1, SEQ ID NO:5, SEQ ID NO:3 and SEQ ID NO:9.

Figure 10:
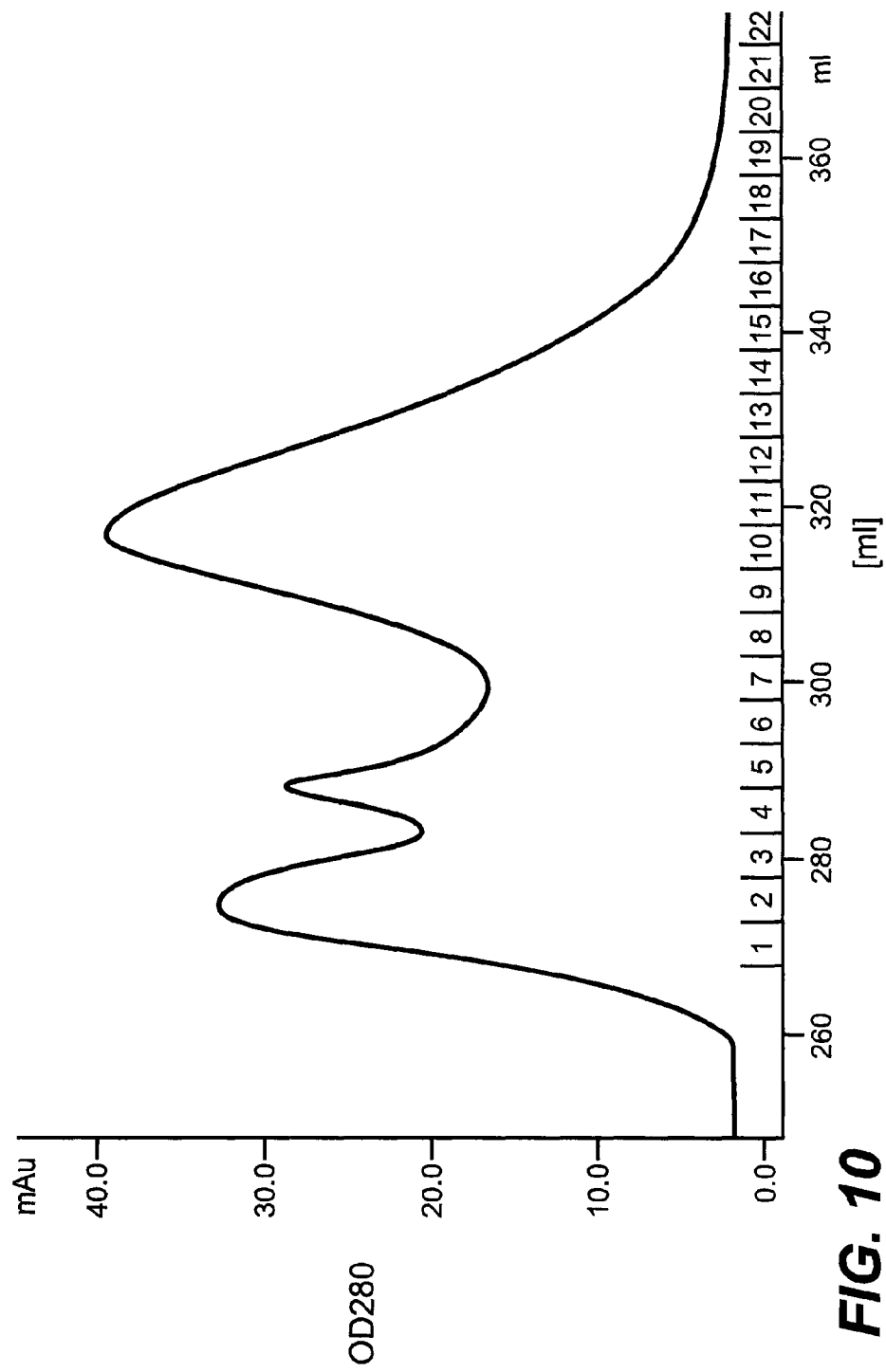
FIG. 10 Size Exclusion Chromatography of a trispecific antibody according to the invention recognizing Angiopoietin-2, VEGF-A and EGFR, which is tetravalent and uses single chain Fab fragments as antigen binding peptides (Example 2) on a high load 26/60 Superdex 200 column.

These antibody variants were generated as described above in the general methods section by classical molecular biology techniques and were expressed transiently in HEK293F cells as described above. Subsequently, they were purified from the supernatant by a combination of Protein A affinity chromatography and size exclusion chromatography. The obtained products were characterized for identity by mass spectrometry and analytical properties such as purity by SDS-PAGE, monomer content and stability (FIGS. 10-11, base on SEQ ID NO:1, SEQ ID NO:5, SEQ ID NO:3 and SEQ ID NO:9).

(Simultaneous) binding of the four antibody specificities to the three covered antigens (Angiopoietin-2, VEGF-A and EGFR) was shown by Biacore using the methods described above.

TABLE

Binding of trispecific and tetravalent antibody recognizing Angiopoietin-2, VEGF-A, and EGFR according to FIG. 5b.

| Analyte | ka (1/Ms) | kd (1/s) | KD (nM) |
|---|---|---|---|
| EGFR (HER1) | 3.7E+04* | 3.4E−04* | 2.7* |
| Ang-2 | n.d.** | n.d.** | 176** |
| VEGF | 6.7E+04* | <1E−06* | <0.01* |

*Capturing via anti-human antibody
**Ang-2 surface

Example 3

Figure 6:
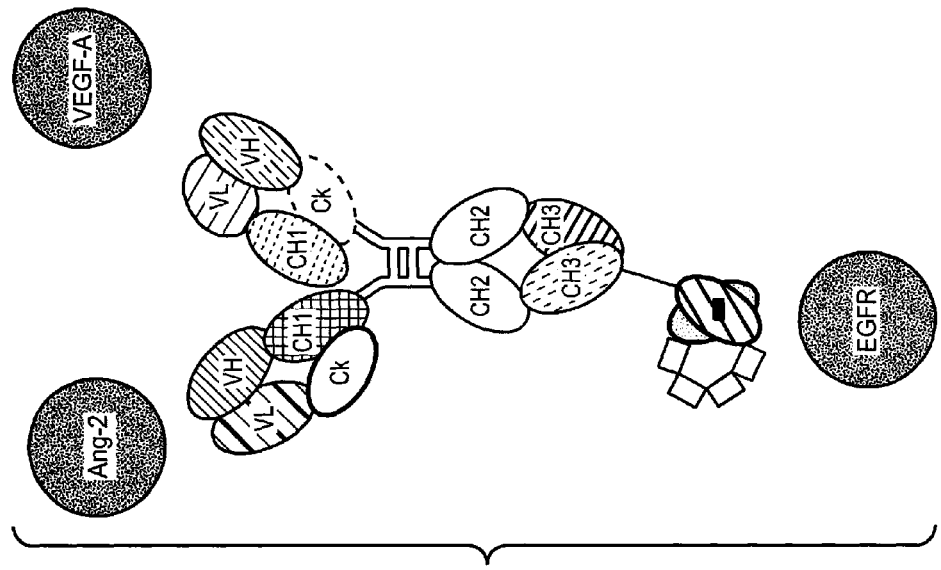
FIG. 6 Schematic structure of a trispecific antibody according to the invention recognizing Angiopoietin-2, VEGF-A and EGFR, which is trivalent and uses disulfide stabilized single chain Fv fragments as antigen binding peptides (Example 3)

Production, Expression, Purification and Characterization of a Trispecific and Trivalent Antibody Recognizing Angiopoietin-2, VEGF-A and EGFR In a first example a trispecific and trivalent antibody recognizing Angiopoietin-2, VEGF-A, EGFR and IGF-1R was made by fusing via a (G4S)4-connector a disulfide stabilized scFv against EGFR to the C-termini part of the two heavy chains of a CH1/CL(Ckappa) domain exchanged antibody with knobs-into-holes recognizing Angiopoietin-2 and VEGF with its variable domains (FIG. 6). The sequences of the respective 4 antibody chains are given in SEQ ID NO:1, SEQ ID NO:2, SEQ ID NO:3 and SEQ ID NO:8.

These antibody variant was generated as described above in the general methods section by classical molecular biology techniques and are expressed transiently in HEK293F cells as described above. Subsequently, they are purified from the supernatant by a combination of Protein A affinity chromatography and size exclusion chromatography. The obtained products are characterized for identity by mass spectrometry and analytical properties such as purity by SDS-PAGE, monomer content and stability.

| Key Data | |
| --- | --- |
| Expression (Yield) - mg/mL | 40.9 |
| Purification (Prot. A homogeneity) - % | 77.3 |
| Yield after SEC - mg/mL | 22.3 |
| Homogeneity after preparative SEC - % | 100 |

(Simultaneous) binding of the four antibody specificities to the three covered antigens (Angiopoietin-2, VEGF-A and EGFR) is shown by Biacore using the methods described above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A trispecific or tetraspecific antibody, comprising:
   a) a light chain comprising a light chain variable domain VL and a light chain constant domain CL, and a heavy chain comprising a heavy chain variable domain VH and heavy chain constant domains CH1, CH2, and CH3, wherein the light chain and the heavy chain specifically bind to a first antigen; and
   b) a modified light chain and a modified heavy chain that specifically bind to a second antigen, wherein:
      (i) the modified light chain comprises in N-terminal to C-terminal direction VL, CH1, and the modified heavy chain comprises in N-terminal to C-terminal direction VH, CL, CH2, and CH3;
      (ii) the modified light chain comprises in N-terminal to C-terminal direction VH, CL, and the modified heavy chain comprises in N-terminal to C-terminal direction VL, CH1, CH2, and CH3; or
      (iii) the modified light chain comprises in N-terminal to C-terminal direction VH, CH1, and the modified heavy chain comprises in N-terminal to C-terminal direction VL, CL, CH2, and CH3;
   and
   c) one to four antigen binding peptides fused via a peptide connector to the C- or N-terminus of the light chains or heavy chains of a) and/or b) wherein said antigen binding peptides specifically bind one or two further antigens.

2. The antibody according to claim 1, wherein the antigen binding peptides comprise one or two antigen binding peptides which specifically bind to one or two further antigens.

3. The antibody according to claim 1, wherein the antigen binding peptides comprise one or two antigen binding peptides which specifically bind to a third antigen.

4. The antibody according to claim 1, wherein the antigen binding peptides comprise two identical antigen binding peptides which specifically bind to a third antigen.

5. The antibody according to claim 1, wherein the antigen binding peptides comprise one antigen binding peptide which specifically binds to a third antigen and one other antigen binding peptide which specifically binds to a fourth antigen.

6. The antibody according to claim 1, wherein the antigen binding peptides are selected from the group consisting of a scFv fragment and a scFab fragment.

7. The antibody according to claim 1, wherein the antigen binding peptides are scFv fragments.

8. The antibody according to claim 1, wherein the antigen binding peptides are scFab fragments.

9. The antibody according to claim 1, wherein the antigen binding peptides are fused to the C-terminus of the heavy chains of a) and/or b).

10. The antibody according to claim 1, wherein the CH3 domain of the heavy chain of a) and the CH3 domain of the modified heavy chain of b) meet at an interface which has been altered to promote the formation of the trispecific or tetraspecific antibody, wherein the interface of one CH3 domain comprises a protuberance which is positionable in a cavity in the interface of the other CH3 domain, and wherein said interface is altered such that:
    i) the CH3 domain of one heavy chain is altered, so that within the original interface the CH3 domain of the one heavy chain that meets the original interface of the CH3 domain of the other heavy chain, an amino acid residue is replaced with an amino acid residue having a larger side chain volume, thereby generating a protuberance within the interface of the CH3 domain of the one heavy chain, said protuberance being positionable in a cavity within the interface of the CH3 domain of the other heavy chain; and
    ii) the CH3 domain of the other heavy chain is altered, so that within the original interface of the CH3 domain of the other heavy chain that meets the original interface of the CH3 domain of the one heavy chain, an amino acid residue is replaced with an amino acid residue having a smaller side chain volume, thereby generating a cavity within the interface of the CH3 domain of the other heavy chain, said cavity being positionable in a protuberance within the interface of the CH3 domain of the one heavy chain.

11. The antibody according to claim 10, wherein said amino acid residue having a larger side chain volume is selected from the group consisting of arginine (R), phenylalanine (F), tyrosine (Y), tryptophan (W) and said amino acid residue having a smaller side chain volume is selected from the group consisting of alanine (A), serine (S), threonine (T), valine (V).

12. The antibody of claim 10 wherein the protuberance comprises an introduced arginine (R) residue.

13. The antibody of claim 10 wherein the protuberance comprises an introduced phenylalanine (F) residue.

14. The antibody of claim 10 wherein the protuberance comprises an introduced tyrosine (Y) residue.

15. The antibody of claim 10 wherein the protuberance comprises an introduced tryptophan (W) residue.

16. The antibody of claim 10 wherein the cavity is formed by an introduced alanine (A) residue.

17. The antibody of claim 10 wherein the cavity is formed by an introduced serine (S) residue.

18. The antibody of claim 10 wherein the cavity is formed by an introduced threonine (T) residue.

19. The antibody of claim 10 wherein the cavity is formed by an introduced valine (V) residue.

20. The antibody according to claim 10, characterized in that both CH3 domains are further altered by the introduction of a cysteine (C) residue in the corresponding positions of each CH3 domain such that a disulfide bridge between both CH3 domains can be formed.

21. A composition, comprising the antibody according to claim 1.

22. The composition according to claim 21 wherein the composition is a pharmaceutical or diagnostic composition.

23. A pharmaceutical composition comprising an antibody according to claim 1 and at least one pharmaceutically acceptable excipient.

24. The antibody according to claim 1, wherein the modified light chain comprises in N-terminal to C-terminal direction VL, CH1, and the modified heavy chain comprises in N-terminal to C-terminal direction VH, CL, CH2, and CH3.

25. The antibody according to claim 1, wherein the modified light chain comprises in N-terminal to C-terminal direction VH, CL, and the modified heavy chain comprises in N-terminal to C-terminal direction VL, CH1, CH2, and CH3.

26. The antibody according to claim 1, wherein the modified light chain comprises in N-terminal to C-terminal direction VH, CH1, and the modified heavy chain comprises in N-terminal to C-terminal direction VL, CL, CH2, and CH3.

* * * * *

UNITED STATES PATENT AND TRADEMARK OFFICE
CERTIFICATE OF CORRECTION

| | | |
|---|---|---|
| PATENT NO. | : 8,796,424 B2 | Page 1 of 1 |
| APPLICATION NO. | : 12/788967 | |
| DATED | : August 5, 2014 | |
| INVENTOR(S) | : Croasdale et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this
Eleventh Day of August, 2015

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 215
<212> TYPE: PRT
<213> ORGANISM: Artificial
<220> FEATURE:
<223> OTHER INFORMATION: light chain <Ang-2>

<400> SEQUENCE: 1

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

Ser Phe Asn Arg Gly Glu Cys
    210                 215

<210> SEQ ID NO 2
<211> LENGTH: 725
<212> TYPE: PRT
<213> ORGANISM: Artificial
<220> FEATURE:
<223> OTHER INFORMATION: knobs-heavy chain <Ang-2> with C-terminal fused
      <EGFR> scFv

<400> SEQUENCE: 2

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys

```
                340                 345                 350
Gly Gln Pro Arg Glu Pro Gln Val Tyr Thr Leu Pro Pro Cys Arg Asp
            355                 360                 365
Glu Leu Thr Lys Asn Gln Val Ser Leu Trp Cys Leu Val Lys Gly Phe
        370                 375                 380
Tyr Pro Ser Asp Ile Ala Val Glu Trp Glu Ser Asn Gly Gln Pro Glu
385                 390                 395                 400
Asn Asn Tyr Lys Thr Thr Pro Pro Val Leu Asp Ser Asp Gly Ser Phe
                405                 410                 415
Phe Leu Tyr Ser Lys Leu Thr Val Asp Lys Ser Arg Trp Gln Gln Gly
            420                 425                 430
Asn Val Phe Ser Cys Ser Val Met His Glu Ala Leu His Asn His Tyr
        435                 440                 445
Thr Gln Lys Ser Leu Ser Leu Ser Pro Gly Lys Gly Gly Gly Gly Ser
    450                 455                 460
Gly Gly Gly Gly Ser Gly Gly Gly Ser Gly Gly Gly Gly Ser Gln
465                 470                 475                 480
Val Gln Leu Val Gln Ser Gly Ala Glu Val Lys Lys Pro Gly Ser Ser
                485                 490                 495
Val Lys Val Ser Cys Lys Ala Ser Gly Phe Thr Phe Thr Asp Tyr Lys
            500                 505                 510
Ile His Trp Val Arg Gln Ala Pro Gly Gln Cys Leu Glu Trp Met Gly
        515                 520                 525
Tyr Phe Asn Pro Asn Ser Gly Tyr Ser Thr Tyr Ala Gln Lys Phe Gln
    530                 535                 540
Gly Arg Val Thr Ile Thr Ala Asp Lys Ser Thr Ser Thr Ala Tyr Met
545                 550                 555                 560
Glu Leu Ser Ser Leu Arg Ser Glu Asp Thr Ala Val Tyr Tyr Cys Ala
                565                 570                 575
Arg Leu Ser Pro Gly Gly Tyr Tyr Val Met Asp Ala Trp Gly Gln Gly
            580                 585                 590
Thr Thr Val Thr Val Ser Ser Gly Gly Gly Ser Gly Gly Gly Gly
        595                 600                 605
Ser Gly Gly Gly Gly Ser Gly Gly Gly Ser Asp Ile Gln Met Thr
    610                 615                 620
Gln Ser Pro Ser Ser Leu Ser Ala Ser Val Gly Asp Arg Val Thr Ile
625                 630                 635                 640
Thr Cys Arg Ala Ser Gln Gly Ile Asn Asn Tyr Leu Asn Trp Tyr Gln
                645                 650                 655
Gln Lys Pro Gly Lys Ala Pro Lys Arg Leu Ile Tyr Asn Thr Asn Asn
            660                 665                 670
Leu Gln Thr Gly Val Pro Ser Arg Phe Ser Gly Ser Gly Ser Gly Thr
        675                 680                 685
Glu Phe Thr Leu Thr Ile Ser Ser Leu Gln Pro Glu Asp Phe Ala Thr
    690                 695                 700
Tyr Tyr Cys Leu Gln His Asn Ser Phe Pro Thr Phe Gly Cys Gly Thr
705                 710                 715                 720
Lys Leu Glu Ile Lys
            725

<210> SEQ ID NO 3
<211> LENGTH: 212
<212> TYPE: PRT
<213> ORGANISM: Artificial
```

<220> FEATURE:
<223> OTHER INFORMATION: light chain <VEGF> with CH1-CL exchange

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
    210
```

<210> SEQ ID NO 4
<211> LENGTH: 718
<212> TYPE: PRT
<213> ORGANISM: Artificial
<220> FEATURE:
<223> OTHER INFORMATION: holes-heavy chain <VEGF> with CH1-CL exchange
      and C-terminal fused <IGF-1R> scFv

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110
```

-continued

```
Trp Gly Gln Gly Thr Leu Val Thr Val Ser Ser Ala Ser Val Ala Ala
            115                 120                 125
Pro Ser Val Phe Ile Phe Pro Ser Asp Glu Gln Leu Lys Ser Gly
130                 135                 140
Thr Ala Ser Val Val Cys Leu Leu Asn Asn Phe Tyr Pro Arg Glu Ala
145                 150                 155                 160
Lys Val Gln Trp Lys Val Asp Asn Ala Leu Gln Ser Gly Asn Ser Gln
                165                 170                 175
Glu Ser Val Thr Glu Gln Asp Ser Lys Asp Ser Thr Tyr Ser Leu Ser
            180                 185                 190
Ser Thr Leu Thr Leu Ser Lys Ala Asp Tyr Glu Lys His Lys Val Tyr
        195                 200                 205
Ala Cys Glu Val Thr His Gln Gly Leu Ser Ser Pro Val Thr Lys Ser
    210                 215                 220
Phe Asn Arg Gly Glu Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
                245                 250                 255
Pro Lys Asp Thr Leu Met Ile Ser Arg Thr Pro Glu Val Thr Cys Val
            260                 265                 270
Val Val Asp Val Ser His Glu Asp Pro Glu Val Lys Phe Asn Trp Tyr
        275                 280                 285
Val Asp Gly Val Glu Val His Asn Ala Lys Thr Lys Pro Arg Glu Glu
    290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Ala Leu Pro Ala Pro Ile Glu Lys Thr Ile Ser Lys Ala Lys Gly Gln
            340                 345                 350
Pro Arg Glu Pro Gln Val Cys Thr Leu Pro Pro Ser Arg Asp Glu Leu
        355                 360                 365
Thr Lys Asn Gln Val Ser Leu Ser Cys Ala Val Lys Gly Phe Tyr Pro
    370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Val Ser Lys Leu Thr Val Asp Lys Ser Arg Trp Gln Gln Gly Asn Val
            420                 425                 430
Phe Ser Cys Ser Val Met His Glu Ala Leu His Asn His Tyr Thr Gln
        435                 440                 445
Lys Ser Leu Ser Leu Ser Pro Gly Lys Gly Gly Gly Ser Gly Gly
    450                 455                 460
Gly Gly Ser Gly Gly Gly Gly Ser Gly Gly Gly Gly Ser Gln Val Glu
465                 470                 475                 480
Leu Val Glu Ser Gly Gly Gly Val Val Gln Pro Gly Arg Ser Gln Arg
                485                 490                 495
Leu Ser Cys Ala Ala Ser Gly Phe Thr Phe Ser Ser Tyr Gly Met His
            500                 505                 510
Trp Val Arg Gln Ala Pro Gly Lys Cys Leu Glu Trp Val Ala Ile Ile
        515                 520                 525
Trp Phe Asp Gly Ser Ser Thr Tyr Tyr Ala Asp Ser Val Arg Gly Arg
```

```
                530                 535                 540
Phe Thr Ile Ser Arg Asp Asn Ser Lys Asn Thr Leu Tyr Leu Gln Met
545                 550                 555                 560

Asn Ser Leu Arg Ala Glu Asp Thr Ala Val Tyr Phe Cys Ala Arg Glu
                565                 570                 575

Leu Gly Arg Arg Tyr Phe Asp Leu Trp Gly Arg Gly Thr Leu Val Ser
                580                 585                 590

Val Ser Ser Gly Gly Gly Gly Ser Gly Gly Gly Ser Gly Gly Gly
            595                 600                 605

Gly Ser Glu Ile Val Leu Thr Gln Ser Pro Ala Thr Leu Ser Leu Ser
            610                 615                 620

Pro Gly Glu Arg Ala Thr Leu Ser Cys Arg Ala Ser Gln Ser Val Ser
625                 630                 635                 640

Ser Tyr Leu Ala Trp Tyr Gln Gln Lys Pro Gly Gln Ala Pro Arg Leu
                645                 650                 655

Leu Ile Tyr Asp Ala Ser Lys Arg Ala Thr Gly Ile Pro Ala Arg Phe
                660                 665                 670

Ser Gly Ser Gly Ser Gly Thr Asp Phe Thr Leu Thr Ile Ser Ser Leu
            675                 680                 685

Glu Pro Glu Asp Phe Ala Val Tyr Tyr Cys Gln Gln Arg Ser Lys Trp
            690                 695                 700

Pro Pro Trp Thr Phe Gly Cys Gly Thr Lys Val Glu Ser Lys
705                 710                 715

<210> SEQ ID NO 5
<211> LENGTH: 941
<212> TYPE: PRT
<213> ORGANISM: Artificial
<220> FEATURE:
<223> OTHER INFORMATION: knobs-heavy chain <Ang-2> with C-terminal fused
      <EGFR> scFab

<400> SEQUENCE: 5

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Thr Lys Gly Pro Ser Val Phe Pro Leu Ala Pro Ser Ser
130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175
```

-continued

```
Ser Gly Val His Thr Phe Pro Ala Val Leu Gln Ser Ser Gly Leu Tyr
            180                 185                 190
Ser Leu Ser Ser Val Val Thr Val Pro Ser Ser Ser Leu Gly Thr Gln
        195                 200                 205
Thr Tyr Ile Cys Asn Val Asn His Lys Pro Ser Asn Thr Lys Val Asp
    210                 215                 220
Lys Lys Val Glu Pro Lys Ser Cys Asp Lys Thr His Thr Cys Pro Pro
225                 230                 235                 240
Cys Pro Ala Pro Glu Leu Leu Gly Gly Pro Ser Val Phe Leu Phe Pro
                245                 250                 255
Pro Lys Pro Lys Asp Thr Leu Met Ile Ser Arg Thr Pro Glu Val Thr
            260                 265                 270
Cys Val Val Val Asp Val Ser His Glu Asp Pro Glu Val Lys Phe Asn
        275                 280                 285
Trp Tyr Val Asp Gly Val Glu Val His Asn Ala Lys Thr Lys Pro Arg
    290                 295                 300
Glu Glu Gln Tyr Asn Ser Thr Tyr Arg Val Val Ser Val Leu Thr Val
305                 310                 315                 320
Leu His Gln Asp Trp Leu Asn Gly Lys Glu Tyr Lys Cys Lys Val Ser
                325                 330                 335
Asn Lys Ala Leu Pro Ala Pro Ile Glu Lys Thr Ile Ser Lys Ala Lys
            340                 345                 350
Gly Gln Pro Arg Glu Pro Gln Val Tyr Thr Leu Pro Pro Cys Arg Asp
        355                 360                 365
Glu Leu Thr Lys Asn Gln Val Ser Leu Trp Cys Leu Val Lys Gly Phe
    370                 375                 380
Tyr Pro Ser Asp Ile Ala Val Glu Trp Glu Ser Asn Gly Gln Pro Glu
385                 390                 395                 400
Asn Asn Tyr Lys Thr Thr Pro Pro Val Leu Asp Ser Asp Gly Ser Phe
                405                 410                 415
Phe Leu Tyr Ser Lys Leu Thr Val Asp Lys Ser Arg Trp Gln Gln Gly
            420                 425                 430
Asn Val Phe Ser Cys Ser Val Met His Glu Ala Leu His Asn His Tyr
        435                 440                 445
Thr Gln Lys Ser Leu Ser Leu Ser Pro Gly Lys Gly Gly Gly Gly Ser
    450                 455                 460
Gly Gly Gly Gly Ser Asp Ile Gln Met Thr Gln Ser Pro Ser Ser Leu
465                 470                 475                 480
Ser Ala Ser Val Gly Asp Arg Val Thr Ile Thr Cys Arg Ala Ser Gln
                485                 490                 495
Gly Ile Asn Asn Tyr Leu Asn Trp Tyr Gln Gln Lys Pro Gly Lys Ala
            500                 505                 510
Pro Lys Arg Leu Ile Tyr Asn Thr Asn Asn Leu Gln Thr Gly Val Pro
        515                 520                 525
Ser Arg Phe Ser Gly Ser Gly Ser Gly Thr Glu Phe Thr Leu Thr Ile
    530                 535                 540
Ser Ser Leu Gln Pro Glu Asp Phe Ala Thr Tyr Tyr Cys Leu Gln His
545                 550                 555                 560
Asn Ser Phe Pro Thr Phe Gly Cys Gly Thr Lys Leu Glu Ile Lys Arg
                565                 570                 575
Thr Val Ala Ala Pro Ser Val Phe Ile Phe Pro Pro Ser Asp Glu Gln
            580                 585                 590
Leu Lys Ser Gly Thr Ala Ser Val Val Cys Leu Leu Asn Asn Phe Tyr
```

```
                    595                 600                 605
Pro Arg Glu Ala Lys Val Gln Trp Lys Val Asp Asn Ala Leu Gln Ser
    610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
                645                 650                 655

His Lys Val Tyr Ala Cys Glu Val Thr His Gln Gly Leu Ser Ser Pro
            660                 665                 670

Val Thr Lys Ser Phe Asn Arg Gly Glu Cys Gly Gly Gly Ser Gly
        675                 680                 685

Gly Gly Ser Gly Gly Gly Ser Gly Gly Gly Ser Gly Gly
    690                 695                 700

Gly Gly Ser Gly Gly Gly Ser Gly Gln Val Gln Leu Val Gln
705                 710                 715                 720

Ser Gly Ala Glu Val Lys Lys Pro Gly Ser Ser Val Lys Val Ser Cys
                725                 730                 735

Lys Ala Ser Gly Phe Thr Phe Thr Asp Tyr Lys Ile His Trp Val Arg
            740                 745                 750

Gln Ala Pro Gly Gln Cys Leu Glu Trp Met Gly Tyr Phe Asn Pro Asn
        755                 760                 765

Ser Gly Tyr Ser Thr Tyr Ala Gln Lys Phe Gln Gly Arg Val Thr Ile
770                 775                 780

Thr Ala Asp Lys Ser Thr Ser Thr Ala Tyr Met Glu Leu Ser Ser Leu
785                 790                 795                 800

Arg Ser Glu Asp Thr Ala Val Tyr Tyr Cys Ala Arg Leu Ser Pro Gly
                805                 810                 815

Gly Tyr Tyr Val Met Asp Ala Trp Gly Gln Gly Thr Thr Val Thr Val
            820                 825                 830

Ser Ser Ala Ser Thr Lys Gly Pro Ser Val Phe Pro Leu Ala Pro Ser
        835                 840                 845

Ser Lys Ser Thr Ser Gly Gly Thr Ala Ala Leu Gly Cys Leu Val Lys
850                 855                 860

Asp Tyr Phe Pro Glu Pro Val Thr Val Ser Trp Asn Ser Gly Ala Leu
865                 870                 875                 880

Thr Ser Gly Val His Thr Phe Pro Ala Val Leu Gln Ser Ser Gly Leu
                885                 890                 895

Tyr Ser Leu Ser Ser Val Val Thr Val Pro Ser Ser Ser Leu Gly Thr
            900                 905                 910

Gln Thr Tyr Ile Cys Asn Val Asn His Lys Pro Ser Asn Thr Lys Val
        915                 920                 925

Asp Lys Lys Val Glu Pro Lys Ser Cys Asp Lys Thr His
930                 935                 940

<210> SEQ ID NO 6
<211> LENGTH: 939
<212> TYPE: PRT
<213> ORGANISM: Artificial
<220> FEATURE:
<223> OTHER INFORMATION: holes-heavy chain <VEGF> with CH1-CL exchange
      and C-terminal fused <IGF-1R> scFab

<400> SEQUENCE: 6

Glu Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Val Ala Ala
        115                 120                 125

Pro Ser Val Phe Ile Phe Pro Pro Ser Asp Glu Gln Leu Lys Ser Gly
130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
            165                 170                 175

Glu Ser Val Thr Glu Gln Asp Ser Lys Asp Ser Thr Tyr Ser Leu Ser
        180                 185                 190

Ser Thr Leu Thr Leu Ser Lys Ala Asp Tyr Glu Lys His Lys Val Tyr
    195                 200                 205

Ala Cys Glu Val Thr His Gln Gly Leu Ser Ser Pro Val Thr Lys Ser
210                 215                 220

Phe Asn Arg Gly Glu Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
    275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Cys Thr Leu Pro Pro Ser Arg Asp Glu Leu
    355                 360                 365

Thr Lys Asn Gln Val Ser Leu Ser Cys Ala Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Val Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln

```
                    435                 440                 445
        Lys Ser Leu Ser Leu Ser Pro Gly Lys Gly Gly Gly Ser Gly Gly
                    450                 455                 460

Gly Gly Ser Glu Ile Val Leu Thr Gln Ser Pro Ala Thr Leu Ser Leu
        465                 470                 475                 480

Ser Pro Gly Glu Arg Ala Thr Leu Ser Cys Arg Ala Ser Gln Ser Val
                        485                 490                 495

Ser Ser Tyr Leu Ala Trp Tyr Gln Gln Lys Pro Gly Gln Ala Pro Arg
                    500                 505                 510

Leu Leu Ile Tyr Asp Ala Ser Lys Arg Ala Thr Gly Ile Pro Ala Arg
                    515                 520                 525

Phe Ser Gly Ser Gly Ser Gly Thr Asp Phe Thr Leu Thr Ile Ser Ser
        530                 535                 540

Leu Glu Pro Glu Asp Phe Ala Val Tyr Tyr Cys Gln Gln Arg Ser Lys
        545                 550                 555                 560

Trp Pro Pro Trp Thr Phe Gly Cys Gly Thr Lys Val Glu Ser Lys Arg
                        565                 570                 575

Thr Val Ala Ala Pro Ser Val Phe Ile Phe Pro Pro Ser Asp Glu Gln
                    580                 585                 590

Leu Lys Ser Gly Thr Ala Ser Val Val Cys Leu Leu Asn Asn Phe Tyr
                    595                 600                 605

Pro Arg Glu Ala Lys Val Gln Trp Lys Val Asp Asn Ala Leu Gln Ser
                    610                 615                 620

Gly Asn Ser Gln Glu Ser Val Thr Glu Gln Asp Ser Lys Asp Ser Thr
        625                 630                 635                 640

Tyr Ser Leu Ser Ser Thr Leu Thr Leu Ser Lys Ala Asp Tyr Glu Lys
                        645                 650                 655

His Lys Val Tyr Ala Cys Glu Val Thr His Gln Gly Leu Ser Ser Pro
                    660                 665                 670

Val Thr Lys Ser Phe Asn Arg Gly Glu Cys Gly Gly Gly Gly Ser Gly
                    675                 680                 685

Gly Gly Gly Ser Gly Gly Gly Gly Ser Gly Gly Gly Gly Ser Gly Gly
        690                 695                 700

Gly Gly Ser Gly Gly Gly Gly Ser Gly Gly Gln Val Glu Leu Val Glu
        705                 710                 715                 720

Ser Gly Gly Gly Val Val Gln Pro Gly Arg Ser Gln Arg Leu Ser Cys
                        725                 730                 735

Ala Ala Ser Gly Phe Thr Phe Ser Ser Tyr Gly Met His Trp Val Arg
                    740                 745                 750

Gln Ala Pro Gly Lys Cys Leu Glu Trp Val Ala Ile Ile Trp Phe Asp
                    755                 760                 765

Gly Ser Ser Thr Tyr Tyr Ala Asp Ser Val Arg Gly Arg Phe Thr Ile
        770                 775                 780

Ser Arg Asp Asn Ser Lys Asn Thr Leu Tyr Leu Gln Met Asn Ser Leu
        785                 790                 795                 800

Arg Ala Glu Asp Thr Ala Val Tyr Phe Cys Ala Arg Glu Leu Gly Arg
                        805                 810                 815

Arg Tyr Phe Asp Leu Trp Gly Arg Gly Thr Leu Val Ser Val Ser Ser
                    820                 825                 830

Ala Ser Thr Lys Gly Pro Ser Val Phe Pro Leu Ala Pro Ser Ser Lys
                    835                 840                 845

Ser Thr Ser Gly Gly Thr Ala Ala Leu Gly Cys Leu Val Lys Asp Tyr
        850                 855                 860
```

```
Phe Pro Glu Pro Val Thr Val Ser Trp Asn Ser Gly Ala Leu Thr Ser
865                 870                 875                 880

Gly Val His Thr Phe Pro Ala Val Leu Gln Ser Ser Gly Leu Tyr Ser
            885                 890                 895

Leu Ser Ser Val Val Thr Val Pro Ser Ser Ser Leu Gly Thr Gln Thr
                900                 905                 910

Tyr Ile Cys Asn Val Asn His Lys Pro Ser Asn Thr Lys Val Asp Lys
            915                 920                 925

Lys Val Glu Pro Lys Ser Cys Asp Lys Thr His
930                 935

<210> SEQ ID NO 7
<211> LENGTH: 723
<212> TYPE: PRT
<213> ORGANISM: Artificial
<220> FEATURE:
<223> OTHER INFORMATION: holes-heavy chain <VEGF> with CH1-CL exchange
      and C-terminal fused <EGFR> scFv

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Val Ala Ala
        115                 120                 125

Pro Ser Val Phe Ile Phe Pro Pro Ser Asp Glu Gln Leu Lys Ser Gly
130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
            165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
            210                 215                 220

Phe Asn Arg Gly Glu Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
```

```
                275                 280                 285
Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
                340                 345                 350

Pro Arg Glu Pro Gln Val Cys Thr Leu Pro Pro Ser Arg Asp Glu Leu
                355                 360                 365

Thr Lys Asn Gln Val Ser Leu Ser Cys Ala Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Val Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
                435                 440                 445

Lys Ser Leu Ser Leu Ser Pro Gly Lys Gly Gly Gly Ser Gly Gly
450                 455                 460

Gly Gly Ser Gly Gly Gly Ser Gly Gly Gly Ser Gln Val Gln
465                 470                 475                 480

Leu Val Gln Ser Gly Ala Glu Val Lys Lys Pro Gly Ser Ser Val Lys
                485                 490                 495

Val Ser Cys Lys Ala Ser Gly Phe Thr Phe Thr Asp Tyr Lys Ile His
                500                 505                 510

Trp Val Arg Gln Ala Pro Gly Gln Cys Leu Glu Trp Met Gly Tyr Phe
                515                 520                 525

Asn Pro Asn Ser Gly Tyr Ser Thr Tyr Ala Gln Lys Phe Gln Gly Arg
                530                 535                 540

Val Thr Ile Thr Ala Asp Lys Ser Thr Ser Thr Ala Tyr Met Glu Leu
545                 550                 555                 560

Ser Ser Leu Arg Ser Glu Asp Thr Ala Val Tyr Tyr Cys Ala Arg Leu
                565                 570                 575

Ser Pro Gly Gly Tyr Tyr Val Met Asp Ala Trp Gly Gln Gly Thr Thr
                580                 585                 590

Val Thr Val Ser Ser Gly Gly Gly Ser Gly Gly Gly Gly Ser Gly
                595                 600                 605

Gly Gly Gly Ser Gly Gly Gly Ser Asp Ile Gln Met Thr Gln Ser
                610                 615                 620

Pro Ser Ser Leu Ser Ala Ser Val Gly Asp Arg Val Thr Ile Thr Cys
625                 630                 635                 640

Arg Ala Ser Gln Gly Ile Asn Asn Tyr Leu Asn Trp Tyr Gln Gln Lys
                645                 650                 655

Pro Gly Lys Ala Pro Lys Arg Leu Ile Tyr Asn Thr Asn Asn Leu Gln
                660                 665                 670

Thr Gly Val Pro Ser Arg Phe Ser Gly Ser Gly Ser Gly Thr Glu Phe
                675                 680                 685

Thr Leu Thr Ile Ser Ser Leu Gln Pro Glu Asp Phe Ala Thr Tyr Tyr
                690                 695                 700
```

-continued

Cys Leu Gln His Asn Ser Phe Pro Thr Phe Gly Cys Gly Thr Lys Leu
705                 710                 715                 720

Glu Ile Lys

<210> SEQ ID NO 8
<211> LENGTH: 457
<212> TYPE: PRT
<213> ORGANISM: Artificial
<220> FEATURE:
<223> OTHER INFORMATION: holes-heavy chain <VEGF> with CH1-CL exchange

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Val Ala Ala
        115                 120                 125

Pro Ser Val Phe Ile Phe Pro Pro Ser Asp Glu Gln Leu Lys Ser Gly
130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

-continued

```
Ala Leu Pro Ala Pro Ile Glu Lys Thr Ile Ser Lys Ala Lys Gly Gln
                340                 345                 350

Pro Arg Glu Pro Gln Val Cys Thr Leu Pro Pro Ser Arg Asp Glu Leu
            355                 360                 365

Thr Lys Asn Gln Val Ser Leu Ser Cys Ala Val Lys Gly Phe Tyr Pro
        370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Val Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455
```

<210> SEQ ID NO 9
<211> LENGTH: 939
<212> TYPE: PRT
<213> ORGANISM: Artificial
<220> FEATURE:
<223> OTHER INFORMATION: holes-heavy chain <VEGF> with CH1-CL exchange
and C-terminal fused <EGFR> scFab

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys Asp Lys Thr His Thr Cys Pro Pro Cys Pro
225                 230                 235                 240
```

```
Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Cys Thr Leu Pro Pro Ser Arg Asp Glu Leu
    355                 360                 365

Thr Lys Asn Gln Val Ser Leu Ser Cys Ala Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Val Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
        435                 440                 445

Lys Ser Leu Ser Leu Ser Pro Gly Lys Gly Gly Gly Ser Gly Gly
    450                 455                 460

Gly Gly Ser Asp Ile Gln Met Thr Gln Ser Pro Ser Ser Leu Ser Ala
465                 470                 475                 480

Ser Val Gly Asp Arg Val Thr Ile Thr Cys Arg Ala Ser Gln Gly Ile
            485                 490                 495

Asn Asn Tyr Leu Asn Trp Tyr Gln Gln Lys Pro Gly Lys Ala Pro Lys
        500                 505                 510

Arg Leu Ile Tyr Asn Thr Asn Asn Leu Gln Thr Gly Val Pro Ser Arg
    515                 520                 525

Phe Ser Gly Ser Gly Ser Gly Thr Glu Phe Thr Leu Thr Ile Ser Ser
    530                 535                 540

Leu Gln Pro Glu Asp Phe Ala Thr Tyr Tyr Cys Leu Gln His Asn Ser
545                 550                 555                 560

Phe Pro Thr Phe Gly Cys Gly Thr Lys Leu Glu Ile Lys Arg Thr Val
            565                 570                 575

Ala Ala Pro Ser Val Phe Ile Phe Pro Pro Ser Asp Glu Gln Leu Lys
        580                 585                 590

Ser Gly Thr Ala Ser Val Val Cys Leu Leu Asn Asn Phe Tyr Pro Arg
    595                 600                 605

Glu Ala Lys Val Gln Trp Lys Val Asp Asn Ala Leu Gln Ser Gly Asn
    610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
            645                 650                 655
```

```
Val Tyr Ala Cys Glu Val Thr His Gln Gly Leu Ser Ser Pro Val Thr
            660                 665                 670

Lys Ser Phe Asn Arg Gly Glu Cys Gly Gly Gly Ser Gly Gly Gly Gly
        675                 680                 685

Gly Ser Gly Gly Gly Gly Ser Gly Gly Gly Gly Ser Gly Gly Gly Gly
    690                 695                 700

Ser Gly Gly Gly Gly Ser Gly Gly Gln Val Gln Leu Val Gln Ser Gly
705                 710                 715                 720

Ala Glu Val Lys Lys Pro Gly Ser Ser Val Lys Val Ser Cys Lys Ala
                725                 730                 735

Ser Gly Phe Thr Phe Thr Asp Tyr Lys Ile His Trp Val Arg Gln Ala
        740                 745                 750

Pro Gly Gln Cys Leu Glu Trp Met Gly Tyr Phe Asn Pro Asn Ser Gly
    755                 760                 765

Tyr Ser Thr Tyr Ala Gln Lys Phe Gln Gly Arg Val Thr Ile Thr Ala
770                 775                 780

Asp Lys Ser Thr Ser Thr Ala Tyr Met Glu Leu Ser Ser Leu Arg Ser
785                 790                 795                 800

Glu Asp Thr Ala Val Tyr Tyr Cys Ala Arg Leu Ser Pro Gly Gly Tyr
                805                 810                 815

Tyr Val Met Asp Ala Trp Gly Gln Gly Thr Thr Val Thr Val Ser Ser
        820                 825                 830

Ala Ser Thr Lys Gly Pro Ser Val Phe Pro Leu Ala Pro Ser Ser Lys
    835                 840                 845

Ser Thr Ser Gly Gly Thr Ala Ala Leu Gly Cys Leu Val Lys Asp Tyr
850                 855                 860

Phe Pro Glu Pro Val Thr Val Ser Trp Asn Ser Gly Ala Leu Thr Ser
865                 870                 875                 880

Gly Val His Thr Phe Pro Ala Val Leu Gln Ser Ser Gly Leu Tyr Ser
                885                 890                 895

Leu Ser Ser Val Val Thr Val Pro Ser Ser Ser Leu Gly Thr Gln Thr
        900                 905                 910

Tyr Ile Cys Asn Val Asn His Lys Pro Ser Asn Thr Lys Val Asp Lys
    915                 920                 925

Lys Val Glu Pro Lys Ser Cys Asp Lys Thr His
930                 935

<210> SEQ ID NO 10
<211> LENGTH: 941
<212> TYPE: PRT
<213> ORGANISM: Artificial
<220> FEATURE:
<223> OTHER INFORMATION: knobs-heavy chain <Ang-2> with C-terminal fused
      <IGF-1R> scFab

<400> SEQUENCE: 10

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
                 85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
            115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser His Glu Asp Pro Glu Val Lys Phe Asn
            275                 280                 285

Trp Tyr Val Asp Gly Val Glu Val His Asn Ala Lys Thr Lys Pro Arg
        290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
                340                 345                 350

Gly Gln Pro Arg Glu Pro Gln Val Tyr Thr Leu Pro Pro Cys Arg Asp
            355                 360                 365

Glu Leu Thr Lys Asn Gln Val Ser Leu Trp Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
                420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys Gly Gly Gly Gly Ser
    450                 455                 460

Gly Gly Gly Gly Ser Glu Ile Val Leu Thr Gln Ser Pro Ala Thr Leu
465                 470                 475                 480

Ser Leu Ser Pro Gly Glu Arg Ala Thr Leu Ser Cys Arg Ala Ser Gln
                485                 490                 495
```

```
Ser Val Ser Ser Tyr Leu Ala Trp Tyr Gln Lys Pro Gly Gln Ala
            500                 505                 510
Pro Arg Leu Leu Ile Tyr Asp Ala Ser Lys Arg Ala Thr Gly Ile Pro
        515                 520                 525
Ala Arg Phe Ser Gly Ser Gly Ser Gly Thr Asp Phe Thr Leu Thr Ile
    530                 535                 540
Ser Ser Leu Glu Pro Glu Asp Phe Ala Val Tyr Tyr Cys Gln Gln Arg
545                 550                 555                 560
Ser Lys Trp Pro Pro Trp Thr Phe Gly Cys Gly Thr Lys Val Glu Ser
                565                 570                 575
Lys Arg Thr Val Ala Ala Pro Ser Val Phe Ile Phe Pro Pro Ser Asp
            580                 585                 590
Glu Gln Leu Lys Ser Gly Thr Ala Ser Val Val Cys Leu Leu Asn Asn
        595                 600                 605
Phe Tyr Pro Arg Glu Ala Lys Val Gln Trp Lys Val Asp Asn Ala Leu
    610                 615                 620
Gln Ser Gly Asn Ser Gln Glu Ser Val Thr Glu Gln Asp Ser Lys Asp
625                 630                 635                 640
Ser Thr Tyr Ser Leu Ser Ser Thr Leu Thr Leu Ser Lys Ala Asp Tyr
                645                 650                 655
Glu Lys His Lys Val Tyr Ala Cys Glu Val Thr His Gln Gly Leu Ser
            660                 665                 670
Ser Pro Val Thr Lys Ser Phe Asn Arg Gly Glu Cys Gly Gly Gly Gly
        675                 680                 685
Ser Gly Gly Gly Gly Ser Gly Gly Gly Gly Ser Gly Gly Gly Gly Ser
    690                 695                 700
Gly Gly Gly Gly Ser Gly Gly Gly Ser Gly Gly Gln Val Glu Leu
705                 710                 715                 720
Val Glu Ser Gly Gly Gly Val Val Gln Pro Gly Arg Ser Gln Arg Leu
                725                 730                 735
Ser Cys Ala Ala Ser Gly Phe Thr Phe Ser Ser Tyr Gly Met His Trp
            740                 745                 750
Val Arg Gln Ala Pro Gly Lys Cys Leu Glu Trp Val Ala Ile Ile Trp
        755                 760                 765
Phe Asp Gly Ser Ser Thr Tyr Tyr Ala Asp Ser Val Arg Gly Arg Phe
    770                 775                 780
Thr Ile Ser Arg Asp Asn Ser Lys Asn Thr Leu Tyr Leu Gln Met Asn
785                 790                 795                 800
Ser Leu Arg Ala Glu Asp Thr Ala Val Tyr Phe Cys Ala Arg Glu Leu
                805                 810                 815
Gly Arg Arg Tyr Phe Asp Leu Trp Gly Arg Gly Thr Leu Val Ser Val
            820                 825                 830
Ser Ser Ala Ser Thr Lys Gly Pro Ser Val Phe Pro Leu Ala Pro Ser
        835                 840                 845
Ser Lys Ser Thr Ser Gly Gly Thr Ala Ala Leu Gly Cys Leu Val Lys
    850                 855                 860
Asp Tyr Phe Pro Glu Pro Val Thr Val Ser Trp Asn Ser Gly Ala Leu
865                 870                 875                 880
Thr Ser Gly Val His Thr Phe Pro Ala Val Leu Gln Ser Ser Gly Leu
                885                 890                 895
Tyr Ser Leu Ser Ser Val Val Thr Val Pro Ser Ser Ser Leu Gly Thr
            900                 905                 910
Gln Thr Tyr Ile Cys Asn Val Asn His Lys Pro Ser Asn Thr Lys Val
```

|  |  | 915 |  |  | 920 |  |  | 925 |  |
|---|---|---|---|---|---|---|---|---|---|
| Asp | Lys | Lys | Val | Glu | Pro | Lys | Ser | Cys | Asp | Lys | Thr | His |
|  | 930 |  |  |  | 935 |  |  |  | 940 |